US009988417B2

(12) United States Patent
Ferreiro Gil et al.

(10) Patent No.: US 9,988,417 B2
(45) Date of Patent: Jun. 5, 2018

(54) PROCESS FOR THE PREPARATION OF ESTETROL

(71) Applicant: CRYSTAL PHARMA, S.A.U., Boecillo-Valladolid (ES)

(72) Inventors: Juan José Ferreiro Gil, Boecillo-Valladolid (ES); Jesús Miguel Iglesias Retuerto, Boecillo-Valladolid (ES); Francisco Javier Gallo Nieto, Boecillo-Valladolid (ES)

(73) Assignee: Crystal Pharma, S.A.U., Boecillo-Valladolid (ES)

( * ) Notice: Subject to any disclaimer, the term of this patent is extended or adjusted under 35 U.S.C. 154(b) by 0 days. days.

(21) Appl. No.: 15/022,177

(22) PCT Filed: Sep. 17, 2014

(86) PCT No.: PCT/EP2014/069783
§ 371 (c)(1),
(2) Date: Mar. 15, 2016

(87) PCT Pub. No.: WO2015/040051
PCT Pub. Date: Mar. 26, 2015

(65) Prior Publication Data
US 2016/0229885 A1 Aug. 11, 2016

(30) Foreign Application Priority Data
Sep. 18, 2013 (EP) .................. 13382360

(51) Int. Cl.
*C07J 1/00* (2006.01)
*C07J 17/00* (2006.01)

(52) U.S. Cl.
CPC ............. *C07J 1/007* (2013.01); *C07J 1/0077* (2013.01); *C07J 17/00* (2013.01); *Y02P 20/55* (2015.11)

(58) Field of Classification Search
CPC .......... C07J 1/007; C07J 17/00; C07J 1/0077; Y02P 20/55
See application file for complete search history.

(56) References Cited

U.S. PATENT DOCUMENTS

| 4,016,269 A * | 4/1977 | Hofmeister ............ C07J 1/0062 514/172 |
| 2016/0185717 A1* | 6/2016 | Genilloud Rodr Guez ................ C07C 291/10 514/521 |

FOREIGN PATENT DOCUMENTS

| EP | 1 390 039 B1 | 2/2004 |
| EP | 1 390 040 B1 | 2/2004 |
| EP | 1 390 041 B1 | 2/2004 |
| EP | 1 390 042 B1 | 2/2004 |
| EP | 1 446 128 B1 | 8/2004 |
| EP | 1 511 496 B1 | 3/2005 |
| EP | 1 511 498 B1 | 3/2005 |
| EP | 1 526 856 B1 | 5/2005 |
| EP | 1 971 344 B1 | 9/2008 |
| EP | 2 114 412 B1 | 11/2009 |
| WO | 2004/041839 A2 | 5/2004 |
| WO | 2013/012328 A1 | 1/2013 |
| WO | 2013/034780 A2 | 3/2013 |
| WO | 2013/050553 A1 | 4/2013 |

OTHER PUBLICATIONS

Wuts, P.G.M., 2006 "Protection for Phenols and Catechols." Greene's Protective Groups in Organic Synthesis, Fourth Edition: 367-430.*
Cainelli, et al., Synthesis 1989, 45-47.
Cantrall, et al., "The Synthesis of C-15 B-Substittued Estra-1,3,5(10)-trienes", J. Org. Chem., Jan. 1964, 29, 214-217.
Chun, et al., "Stereoselective synthesis of some methyl-substituted steroid hormones and their in vitro cytotoxic activity against human gastric cancer cell line MGC-803", Steroids 75 (2010) 859-869.
Fishman, et al., "Synthesis of Epimeric 15-Hydroxyestriols, New and Potential Metabolites of Estradiol", 15-Hydroxyesteriols, vol. 33, No. 8, Aug. 1968, 3133-3135.
Johnson, et al., "14-Isoestrone Methyl Ether and Its Identity with Totally Synthetic Material", J. Am. Chem. Soc. 1957, 79, 2005-2009.
Kamikubo T., et al., "A New Stereocontrolled Route to(-)-Shikimic Acid", Chemistry Letters 1996, pp. 987-988.
Nambara T., et al., "Syntheses of Estetrol Monoglucuronides", Steroids, vol. 27, No. 1, Jan. 1976, pp. 111-122.
Poirier D., et al., "Synthesis of 17-beta Estradiol Derivatives with N-Butyl, N-Methyl Alkylamide Side Chain at Position 15", Tetrahedron vol. 47, No. 37, pp. 7751-7766, 1991.
Randl S. et al.,, "A Mechanism Switch in Enyne Metathesis Reactions Involving Rearrangemnt: Influence of Heteroatoms in the Propargylic Position", Adv.Synth. Catal. 2002, 344, No. 6 + 7.
Sererennikova, et al., "LVI. Synthesis of alpha-(Octadecen-1-YL)-beta,alpha'-Didodecylglycerol", J. Org. Chem. USSR, vol. 3, 2048-2050 (1967).
Suzuki E., et al., "Synthesis of 15a-hydroxyestrogen 15-N-acetylglucosaminides", Steroids 60:277-284, 1995.

* cited by examiner

*Primary Examiner* — John M Mauro
(74) *Attorney, Agent, or Firm* — Kramer Amado, P.C.

(57) ABSTRACT

The invention relates to a process for obtaining Estetrol or a salt or solvate thereof, the process comprising: a) reacting a compound of formula (IV) or a salt or solvate thereof, wherein $R^1$ is a hydroxyl protecting group selected from a silyl ether, an ether, an ester, a carbamate and a carbonate, and $R^2$ is a hydroxyl protecting group selected from an ether, with an oxidizing agent selected from $OsO_4$ or a source of osmium tetroxide to produce Estetrol or a compound of formula (II) or a salt or solvate thereof wherein $R^1$ is as defined previously; and b) if a compound of formula (II) is obtained in step a), deprotecting said compound to produce Estetrol.

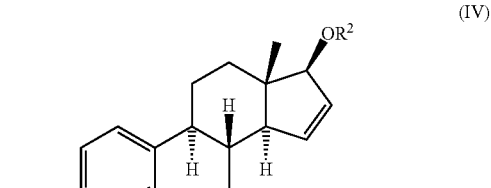

(IV)

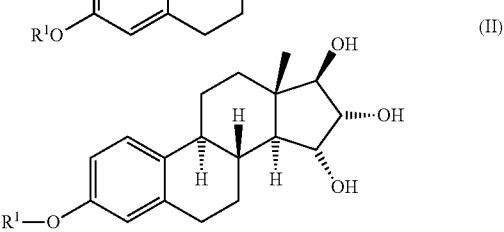

(II)

16 Claims, No Drawings

PROCESS FOR THE PREPARATION OF ESTETROL

FIELD OF THE INVENTION

The invention relates to a process for obtaining Estetrol.

BACKGROUND OF THE INVENTION

Estrogenic substances are commonly used in methods of Hormone Replacement Therapy (HRT) and methods of female contraception. These estrogenic substances can be divided in natural estrogens and synthetic estrogens. Examples of natural estrogens that have found pharmaceutical application include estradiol, estrone, estriol and conjugated equine estrogens. Examples of synthetic estrogens, which offer the advantage of high oral bioavailability include ethinyl estradiol and mestranol.

Estetrol [estra-1,3,5(10)-trien-3,15α,16α,17β-tetraol; CAS Nr. 15183-37-6] is a biogenic estrogen that is endogeneously produced by the fetal liver during human pregnancy. In this description the IUPAC-recommended ring lettering and atom numbering for steroids and steroid derivatives, as depicted below, are applied.

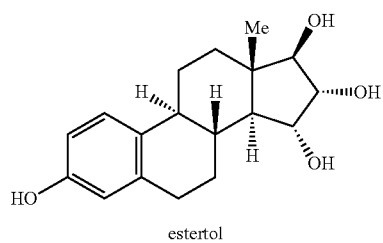

estertol

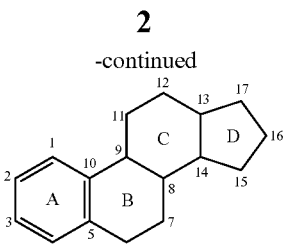

Estetrol has been found effective as an estrogenic substance for use in HRT (EP 1 390 040 B1, EP 1 446 128 B1), contraception (EP 1 390 041 B1, EP 1 390 042 B1), therapy of auto-immune diseases (EP 1 511 496 B1), prevention and therapy of breast and colon tumors (EP 1 526 856 B1), enhancement of libido (EP 1 390 039 B1), treatment of infertility (EP 2 114 412 B1), treatment of acute vascular disorder (EP 1 971 344 B1), skin care and wound healing (EP 1 511 498 A1).

The synthesis of Estetrol on a laboratory scale is for example disclosed in Fishman et al., J. Org. Chem. 1968, 33, 3133-3135, wherein Estetrol is synthesized from estrone derivative III as shown in Scheme 1 (numbering according to Fishman et al).

Scheme 1

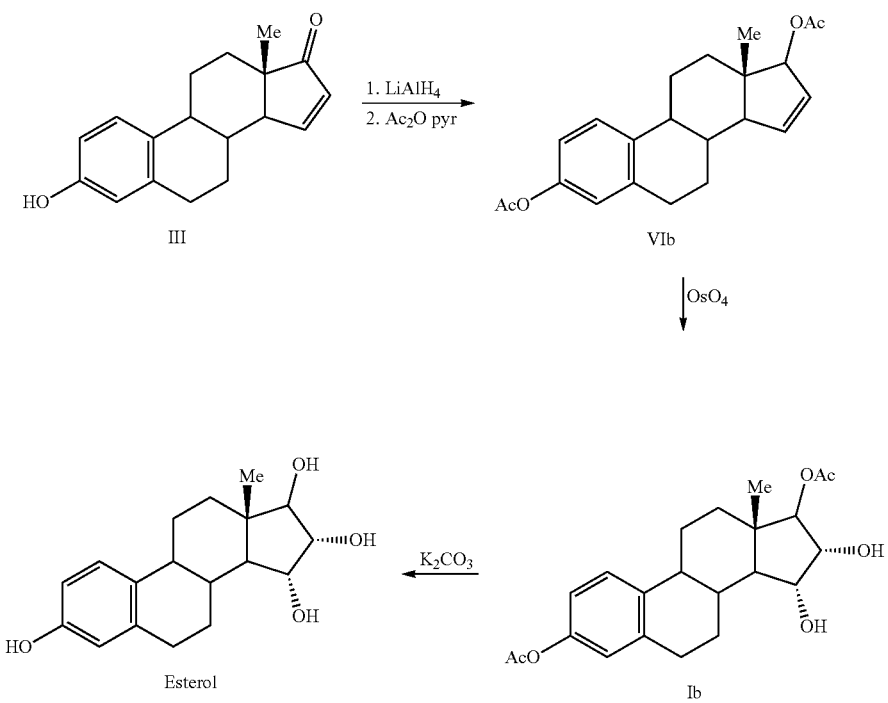

According to Fishman et al., oxidation of the allylic diacetate VIb with OsO$_4$ produced as the desired product Ib together with a small amount of the isomeric 15β,16β-diol. The authors did not quantify the isomeric mixture. The yield of the dihydroxylation is 47% and the overall yield of the 3-step process shown in Scheme 1 is, starting from estrone derivative III, about 7%.

Another synthesis of Estetrol wherein estrone is the starting material is disclosed in Nambara et al., Steroids 1976, 27, 111-121. This synthesis is shown in Scheme 2 compound IVb was hydrolysed by using p-toluene sulfonic acid to compound Vb, followed subsequently by reduction of the carbonyl group at C17 (compound Vc), acetylation (compound Vd) and oxidation of the double bond of ring D thereby forming estra-1,3,5(10)-triene-3,15α,16α,17β-tetraol-3,17-diacetate (compound VIb). Neither experimental protocol nor details about the yield or selectivity of said oxidation of the double bond of ring D are provided in Nambara et al.

Scheme 2

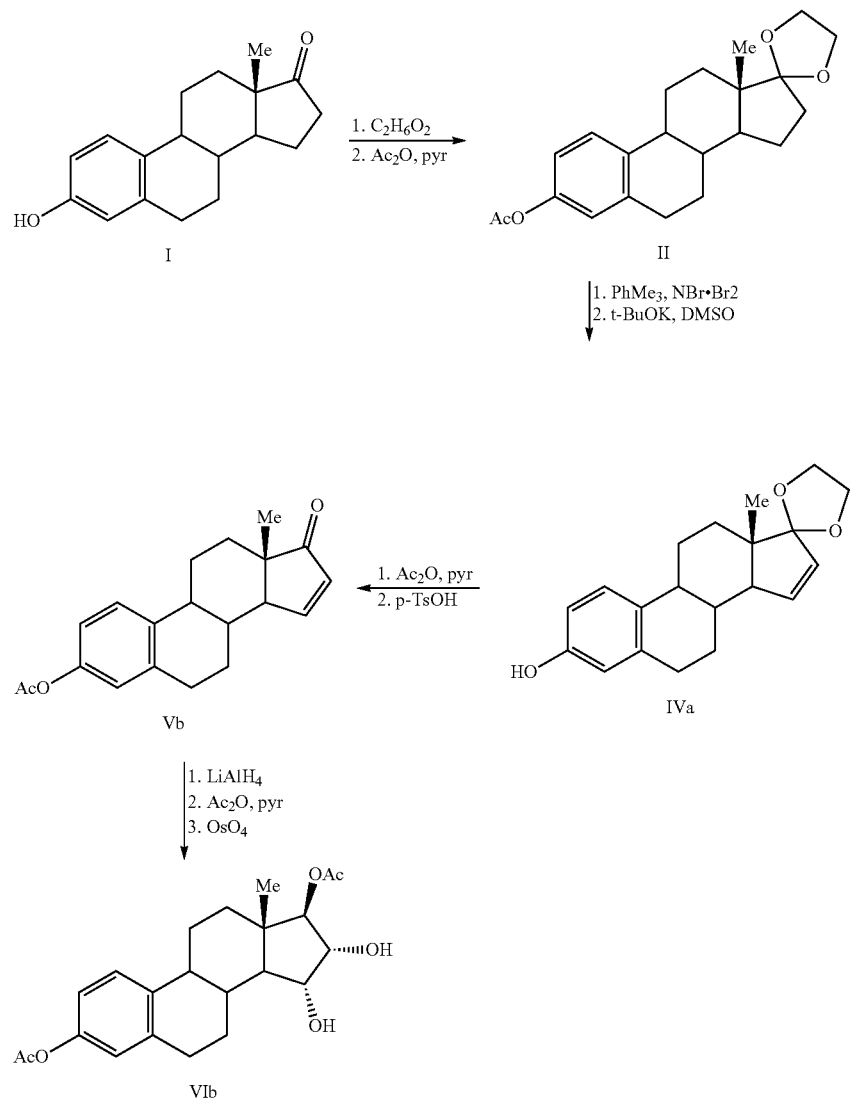

(numbering according to Nambara et al.). The carbonyl group of estrone I is first protected by treatment with ethylene glycol and pyridine hydrochloride followed by acetylation of the hydroxyl group at C3. The next sequence of steps involved a bromination/base catalyzed dehydrobromination resulting into the formation of 17,17-ethylenedioxyestra-1,3,5(10),15-tetraene-3-ol (compound IVa). This compound IVa was subsequently acetylated which produced 17,17-ethylenedioxyestra-1,3,5(10),15-tetraene-3-ol-3-acetate (compound IVb). In a next step, the dioxolane group of Suzuki et al., Steroids 1995, 60, 277-284 also discloses the synthesis of Estetrol by using compound Vb of Nambara et al. as starting material. The carbonyl group at C17 of this compound was first reduced followed by acetylation yielding estra-1,3,5(10),15-tetraene-3,17-diol-3,17-diacetate (compound 2b). The latter was subjected to oxidation with OsO$_4$ which provided estra-1,3,5(10)-triene-3,15α,16α,17β-tetraol-3, 17-diacetate (compound 3b) in 46% yield, along with the isomeric 15β,16β-diol as impurity (15α,16α/15β, 16β isomeric ratio=74/26).

Scheme 3

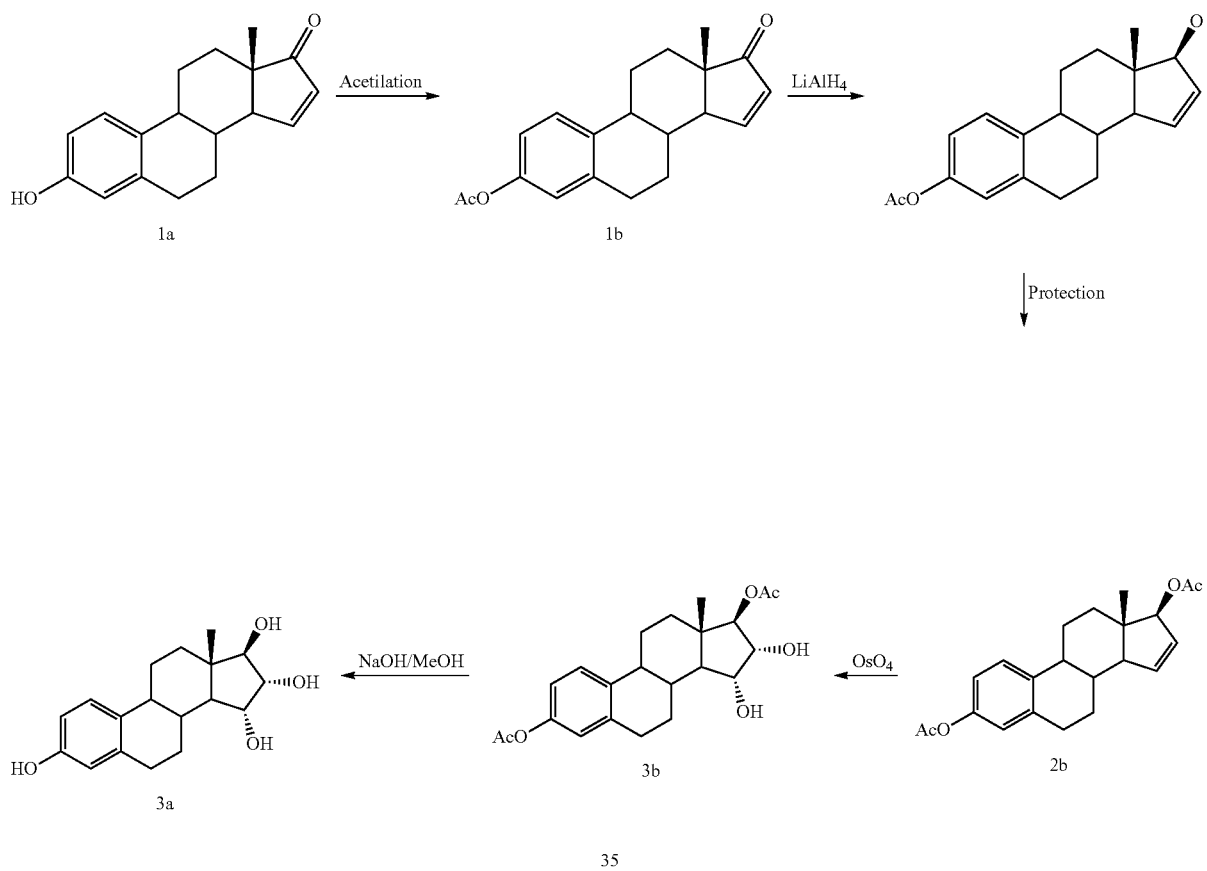

According to Nambara et al. and Suzuki et al., the synthesis of Estetrol can be performed with a yield of approximately 8%, starting from estrone.

A process for the preparation of Estetrol that is suitable for the preparation of this compound on an industrial scale is disclosed in WO 2004/041839 A2. This process is shown in Scheme 4 (numbering according to WO 2004/041839), and comprises the following steps:

1) converting estrone (7) into 3-A-oxy-estra-1,3,5(10),15-tetraen-17-one (6), wherein A is a protecting group, this step involving in turn five sub-steps;
2) reduction of the 17-keto group of 3-A-oxy-estra-1,3,5(10),15-tetraen-17-one (6) to 3-A-oxy-estra-1,3,5(10),15-tetraen-17β-ol (5);
3) protection of the 17-OH group of 3-A-oxy-estra-1,3,5(10),15-tetraen-17β-ol (5) to 3-A-oxy-17-C-oxy-estra-1,3,5(10),15-tetraene (4), wherein C is a protecting group;
4) oxidizing the carbon-carbon double bond of ring D of 3-A-oxy-17-C-oxy-estra-1,3,5(10),15-tetraene (4) to protected Estetrol (3); and
5) removing the protecting groups, wherein preferably protecting group A is removed first to form 17-OC protected Estetrol (2) and subsequently protecting group C is removed to form Estetrol (1);
  wherein the protecting group A is selected from an $C_1$-$C_5$ alkyl group or a $C_7$-$C_{12}$ benzylic group and the protecting group C is selected from monofunctional aliphatic hydroxyl protecting groups.

Scheme 4

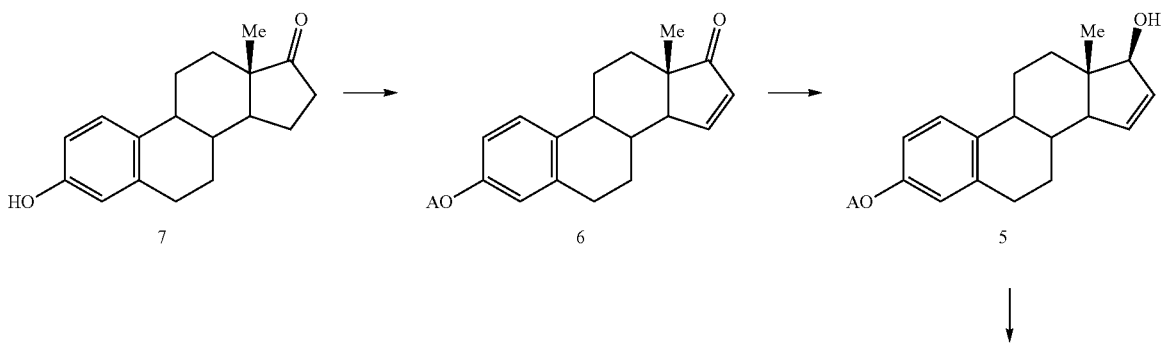

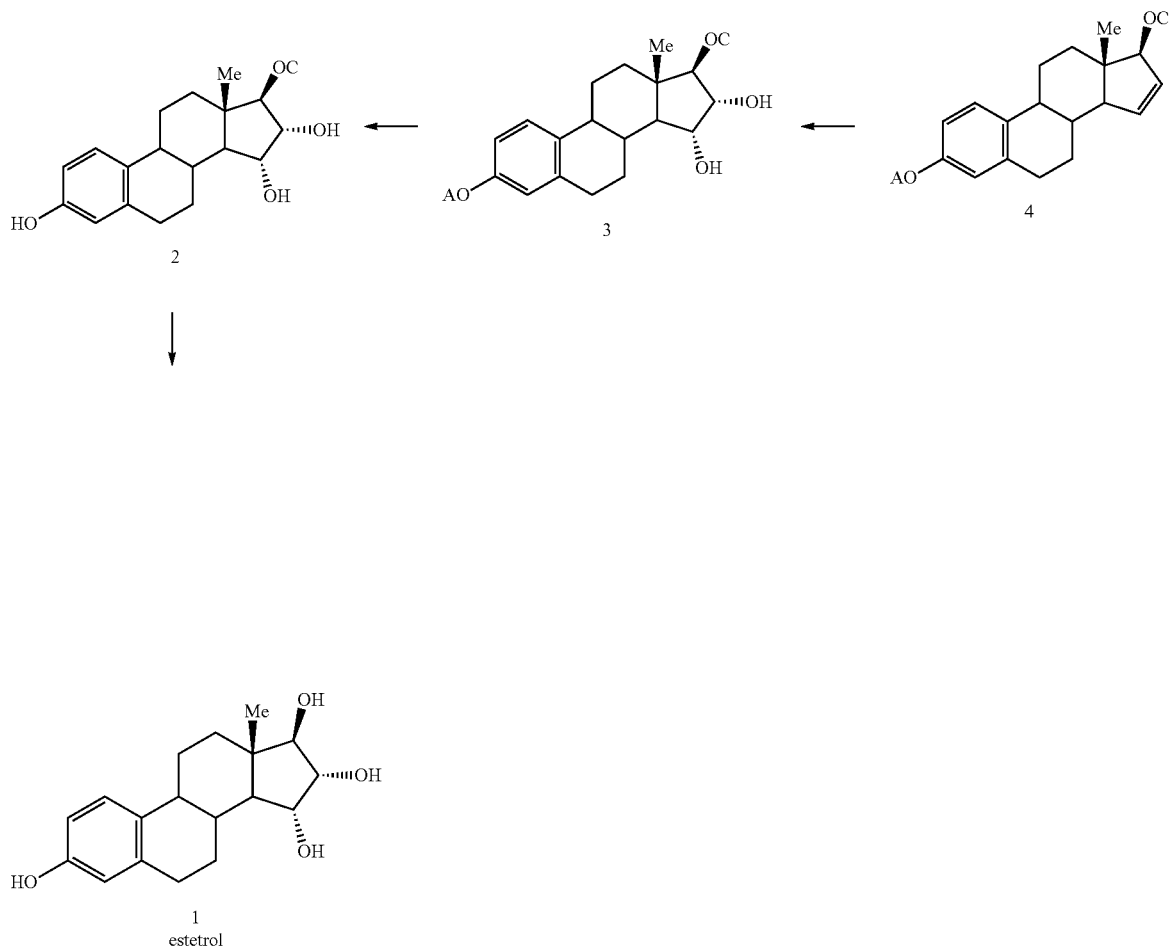

With the method as disclosed in WO 2004/041839 and shown in Scheme 4 above, Estetrol is obtained in an overall yield of 10.8%, starting from estrone. Specifically, the yield of the cis-dihydroxylation step as described in the example 9 is 43% after three crystallizations in order to purify the product from the 15β,16β-diol isomer. Although the process disclosed in WO 2004/041839 is suitable for an industrial scale preparation of Estetrol, the high number of synthetic steps and the isolation and purification of each intermediate product results in a loss of yield, thereby reducing the overall yield of Estetrol. Furthermore, the conversion of 7 into 6 involves a halogenation and a dehalogenation step, typically a bromination and a debromination step. In particular during said halogenation and dehalogenation reactions, various side products are produced.

Another process for the preparation of Estetrol on an industrial scale is disclosed in WO 2013/012328 A1. This process, depicted in Scheme 5 below, comprises the following steps:

(1) conversion of estrone (II) into 17-B-oxy-3-A-oxy-estra-1,3,5(10),16-tetraene (III), wherein A is a protecting group and B is —Si(R²)₃;

(2) conversion of 17-B-oxy-3-A-oxy-estra-1,3,5(10),16-tetraene (III) into 3-A-oxy-estra-1,3,5(10),15-tetraen-17-one (IV), wherein A is a protecting group;

(3) reduction of the 17-keto group of 3-A-oxy-estra-1,3,5(10),15-tetraen-17-one (IV) to form 3-A-oxy-estra-1,3,5(10),15-tetraen-17β-ol (V), wherein A is a protecting group;

(4) protection of the 17-OH group of 3-A-oxy-estra-1,3,5(10),15-tetraen-17β-ol V to form 3-A-oxy-17-C-oxy-estra-1,3,5(10),15-tetraene (VI), wherein A and C are protecting groups;

(5) oxidation of the carbon-carbon double bond of ring D of 3-A-oxy-17-C-oxy-estra-1,3,5(10),15-tetraene (VI) to form protected Estetrol (VII), wherein A and C are protecting groups; and (6) removal of protecting groups A and C to form Estetrol (I);

wherein:

A is a protecting group selected from the group consisting of a $C_1$-$C_5$ alkyl group, a $C_7$-$C_{12}$ benzylic group and a-Si($R^1$)$_3$ group, wherein $R^1$ is independently selected from the group consisting of a $C_1$-$C_6$ alkyl group and a $C_6$-$C_{12}$ aryl group;

B is —Si($R^2$)$_3$, wherein $R^2$ is independently selected from the group consisting of a $C_1$-$C_6$ alkyl group and a $C_6$-$C_{12}$ aryl group; and C is a protecting group selected from the group consisting of monofunctional aliphatic hydroxyl protecting groups.

Scheme 5

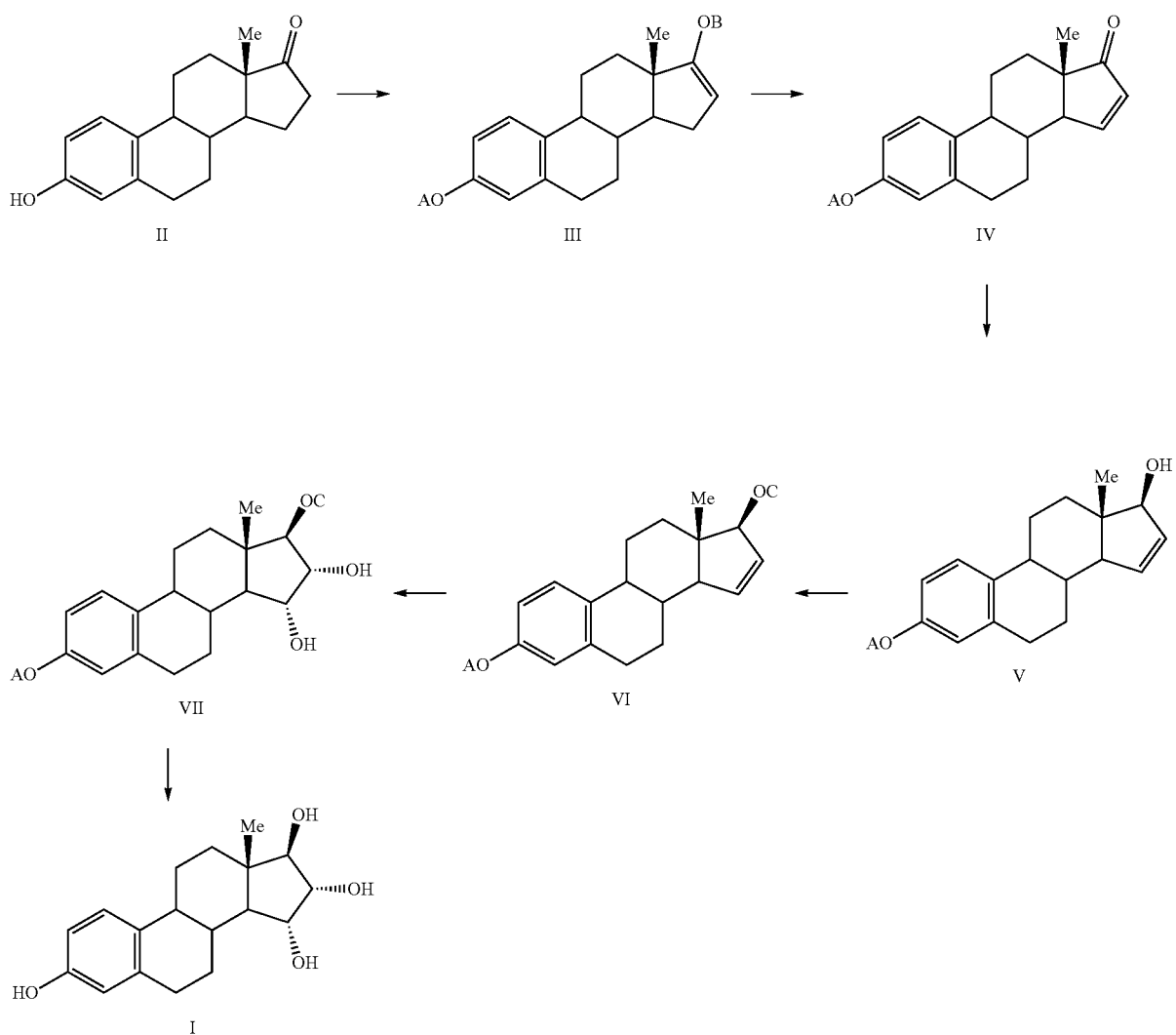

The yield reported for step 5, oxidation of the carbon-carbon double bond from the intermediate product (VI) to form protected Estetrol (VII), is 43% after purifications, with a purity of 98.7%. If a Palladium catalyst is used, the cost of the process increases to a large extent.

WO 2013/034780 A2 discloses a process for obtaining Estetrol and derivatives thereof of formula (I)

-continued

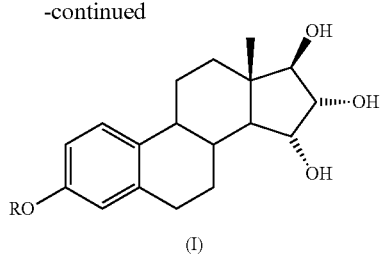

Scheme 6

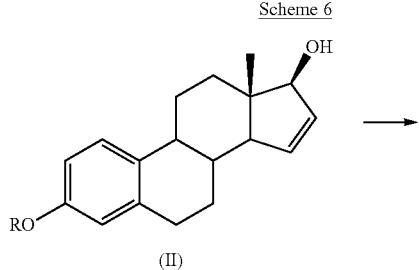

or a salt or solvate thereof, wherein R represents H or an hydroxyl protecting group; the process comprising reacting a compound of formula (II) wherein R is as defined previously, with an oxidizing agent. The process avoids the need of using protecting groups at the β-hydroxyl group at C17, thus simplifying it, and it has been found to provide high stereoselectivities in favor of the desired α,α-isomer as well, on average ≥90%.

WO 2013/050553 A1 discloses a multi-step process for the preparation of Estetrol as depicted in Scheme 7:

Scheme 7

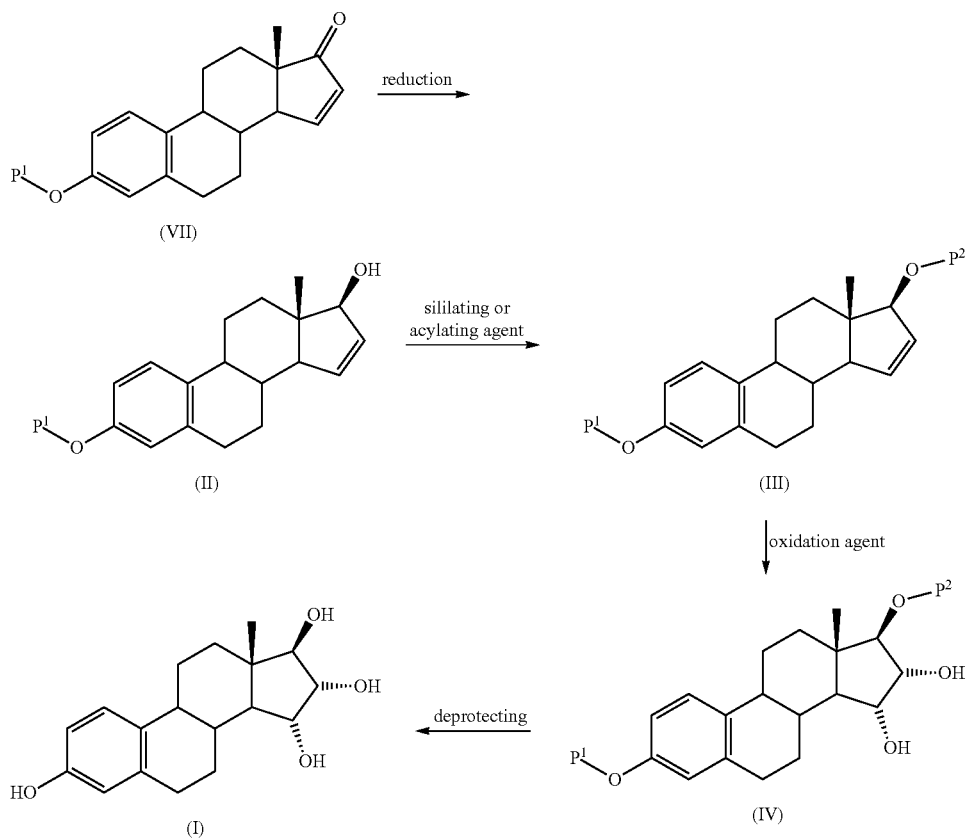

wherein P¹ is a protecting group selected from R¹CO—, or R²Si(R³)(R⁴)—, P² is a protecting group selected from (R⁶R⁵R⁷)C—CO—, or (R²)Si(R³)(R⁴)—, wherein R¹ is a group selected from $C_{1-6}$ alkyl or $C_{3-6}$ cycloalkyl, each group being optionally substituted by one or more substituents independently selected from fluoro or $C_{1-4}$ alkyl; R², R³ and R⁴ are each independently a group selected from $C_{1-6}$ alkyl or phenyl, each group being optionally substituted by one or more substituents independently selected from fluoro or $C_{1-4}$ alkyl; R⁵ is a group selected from $C_{1-6}$ alkyl or phenyl, each group being optionally substituted by one or more substituents independently selected from fluoro or $C_{1-4}$ alkyl; R⁶ and R⁷ are each independently hydrogen or a group selected from $C_{1-6}$ alkyl or phenyl, each group being optionally substituted by one or more substituents independently selected from fluoro or $C_{1-4}$ alkyl.

The disclosed process is alleged to allow the preparation of estra-1,3,5(10)-triene-3,15α,16α,17β-tetrol as the major product with little or no estra-1,3,5(10)-triene-3,15β,16β,17β-tetrol isomer by an oxidation agent selected from KMnO₄, OsO₄, H₂O₂ or I₂/Ag(OAc)₂, but in fact, there are neither data nor examples to support this observation.

When the inventors repeated the procedures disclosed in said application regarding the dihydroxylation reaction to obtain the 15-alpha, 16-alpha diol using KMnO₄ as oxidant (Examples 1 and 2 in WO2013/050553), such product was not observed. In all the cases the starting material was recovered together with 1-2% of the 15-betha, 16-betha diol, instead of the 15-alpha, 16-alpha diol claimed in said patent application (see comparative Examples 1 and 2 in the present application), In most cases the processes disclosed in the state of the art comprise a high number of synthetic steps, affecting the overall yield in which Estetrol is obtained. Further, the oxidation of the carbon-carbon double bond of ring D typically proceeds with a poor or moderate stereoselectivity, obtaining relatively large amounts of the undesired isomeric 15β,16β-diol.

In view of the above, it is still necessary to provide an alternative process for obtaining Estetrol on an industrial scale, which allows the production of this compound in a high yield, and at the same time, minimizes the impurities associated.

SUMMARY OF THE INVENTION

The invention faces the problem of providing an efficient process for the preparation of Estetrol. The inventors have found a process for obtaining Estetrol in very high yield, in which additionally the oxidation (cis-dihydroxilation) of the double bond of ring D proceeds with an exceptional stereoselectivity to afford the desired 15α,16α-diol. The ratio between the 15α,16α-diol and 15β,16β-diol is in many cases 99/1.

Thus, in one aspect the present invention refers to a process for the preparation of a compound of formula (I) (Estetrol)

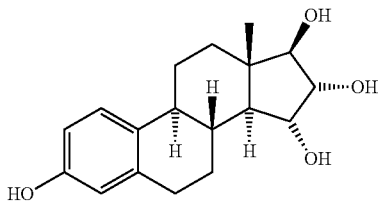
(I)

or a salt or solvate thereof,
the process comprising
a) reacting a compound of formula (IV)

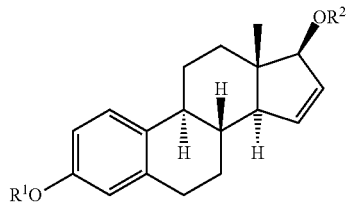
(IV)

or a salt or solvate thereof, wherein
$R^1$ is a hydroxyl protecting group selected from a silyl ether, an ether, an ester, a carbamate and a carbonate, and
$R^2$ is a hydroxyl protecting group selected from an ether,
with an oxidizing agent selected from $OsO_4$ or a source of osmium tetroxide to produce Estetrol or a compound of formula (II) or a salt or solvate thereof

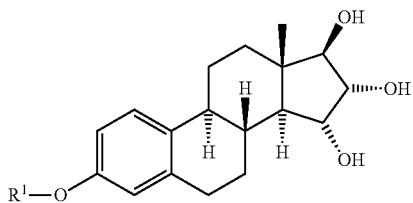
(II)

wherein $R^1$ is as defined previously; and
b) if a compound of formula (II) is obtained in step a), deprotecting said compound to produce Estetrol.

The invention provides an improved process for obtaining Estetrol since deprotection of the ether protecting group at position C17 directly occurs in step a), without the need of adding any reagent. Moreover, in certain cases, typically when the protecting group at C3 is also an ether, which may be the same or different to the ether protecting group at position C17, the protecting group at C3 is cleaved as well in step a), thus allowing the synthesis of Estetrol from the compound of formula (III) in a single synthetic step.

In another aspect, the present invention refers to a compound of formula (IV)

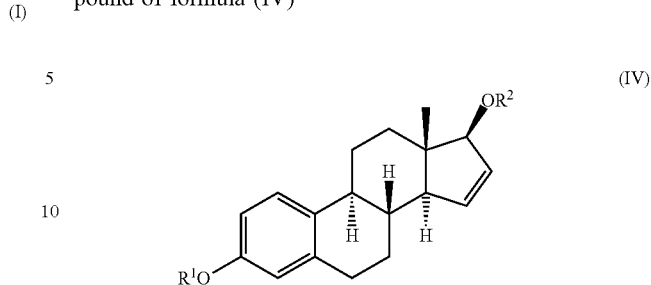
(IV)

or a salt or solvate thereof, wherein
$R^1$ is a hydroxyl protecting group selected from a silyl ether, an ether, an ester, a carbamate and a carbonate, and
$R^2$ is a hydroxyl protecting group selected from an ether, with the proviso that when $R^1$ is methyl then $R^2$ is not a 2-propynyl group nor a 2-tetrahydropyranyl group.

These aspects and preferred embodiments thereof are additionally also defined hereinafter in the detailed description, as well as in the claims.

DETAILED DESCRIPTION OF THE INVENTION

Definitions

In the context of the present invention, the following terms have the meaning detailed below.

As used herein, the term "alkyl" refers to a linear or branched alkane derivative containing from 1 to 6 ("$C_1$-$C_6$ alkyl"), preferably from 1 to 3 ("$C_1$-$C_3$ alkyl"), carbon atoms and which is bound to the rest of the molecule through a single bond. Illustrative examples of alkyl groups include methyl, ethyl, n-propyl, isopropyl, n-butyl, iso-butyl, tert-butyl, pentyl, hexyl, etc.

The term "alkoxy" refers to a radical of the formula —OR where R is an alkyl radical as defined above having one or more (e.g., 1, 2, 3 or 4) oxygen linkages and from 1 to 6 carbon atoms or preferably 1 to 3 carbon atoms, e. g., methoxy, ethoxy, propoxy, etc. The term "aryloxy" refers to a radical of formula —OR wherein R is an aryl radical as defined below, e.g., —O-phenyl, —O-p-tolyl, —O-m-tolyl, —O-o-tolyl or —O-naphthyl.

The term "aryl" refers to an aromatic group having between 6 and 18 ("$C_6$-$C_{18}$ aryl"), preferably between 6 and 10 ("$C_6$-$C_{10}$ aryl"), more preferably 6 or 10 carbon atoms, comprising 1, 2 or 3 aromatic nuclei bound through a carbon-carbon bond or fused to one another. Illustrative examples of aryl groups include phenyl, naphthyl, biphenyl, indenyl, phenanthryl, etc.

Particular examples of substituted alkyl groups are "arylalkyl" and "haloalkyl" groups.

The term "arylalkyl" refers to an alkyl group as defined above substituted with an aryl group as defined above, such as ($C_6$-$C_{18}$)aryl($C_1$-$C_6$)alkyl, ($C_6$-$C_{10}$)aryl($C_1$-$C_6$)alkyl and ($C_6$-$C_{10}$)aryl($C_1$-$C_3$)alkyl. Examples of such groups include benzyl, phenylethyl, phenylpropyl, naphthylmethyl, etc.

The term "haloalkyl" refers to an alkyl group as defined above wherein at least one of the hydrogen atoms has been substituted with a halogen group, for example $CF_3$, $CCl_3$, $CHF_2$, $CF_2CF_3$, etc.

The term "cycloalkyl" refers to a radical derived from cycloalkane containing from 3 to 7 ("$C_3$-$C_7$ cycloalkyl"), preferably from 3 to 6 ("$C_3$-$C_6$ cycloalkyl") carbon atoms.

Illustrative examples of cycloalkyl groups include cyclopropyl, cyclobutyl, cyclopentyl, cyclohexyl, etc.

The term "halogen" refers to bromine, chlorine, iodine or fluorine.

"Heterocyclyl" refers to a stable cyclic radical of 3 to 10 members, preferably a cycle of 5 or 6 members consisting of carbon atoms and from 1 to 5, preferably from 1 to 3, heteroatoms selected from nitrogen, oxygen and sulfur, and which may be completely or partially saturated or be aromatic ("heteroaryl"). In the present invention, the heterocyclyl can be a mono-, bi- or tricyclic system which may include fused ring systems. Illustrative examples of heterocyclyl groups include, for example, pyrrolidine, piperidine, piperazine, morpholine, tetrahydrofuran, benzimidazole, benzothiazole, furan, pyrrole, pyridine, pyrimidine, thiazole, thiophene, imidazole, indole, etc.

As understood in this technical area, there may be a certain degree of substitution in the aforementioned radicals. Therefore, there may be substitution in any of the groups of the present invention. The previous groups can be substituted in one or more available positions with one or more substituents. Said substituents include, for example and in non-limiting sense, alkyl, cycloalkyl, aryl, heterocyclyl, heteroaryl, halogen, —CN, —NO$_2$, —CF$_3$, —N(R)$_2$, —OR', —SR', —C(O)R', —C(O)OR', —C(O)N(R)$_2$, —OC(O)R'; wherein each of the R' groups is independently selected from the group consisting of hydrogen, alkyl, aryl, heterocyclyl, heteroaryl and trifluoromethyl.

The term "hydroxyl protecting group" refers to a group blocking the OH function for subsequent reactions that can be removed under controlled conditions. Hydroxyl protecting groups are well known in the art. Illustrative examples of hydroxyl protecting groups have been described by Green and Wuts. in "Protective Groups in Organic Synthesis", 4th Edition (2007), Ed. John Wiley & Sons (ISBN 0-471-69754-0). Virtually any hydroxyl protecting group can be used to put the invention into practice. Illustrative, non-limiting examples of hydroxyl protecting groups include:

silyl ethers [—Si(R')$_3$], wherein each R' can be independently selected from alkyl, cycloalkyl, aryl, alkoxy and halogen. Examples of silyl ethers include trimethylsilyl ether, triethylsilyl ether, tert-butyldimethylsilyl ether, tert-butyldiphenylsilyl ether, tri-isopropylsilyl ether, diethylisopropylsilyl ether, thexyldimethylsilyl ether, triphenylsilyl ether, di-tert-butylmethylsilyl ether, dimethylphenyl ether;

ethers, including:
  simple ethers [—R'], wherein R can be selected from alkyl, cycloalkyl, aryl and arylalkyl. Examples of ethers include methyl ether, tert-butyl ether, benzyl ether, p-methoxybenzyl ether, 3,4-dimethoxybenzyl ether, trityl ether, allyl ether;
  heteroatom-substituted alkyl ethers including: alkoxy and aryloxy alkyl ethers, such as alkoxy and aryloxy methyl ethers and alkoxy and aryloxy ethyl ethers, as well as alkyl and aryl thioalkyl ethers, such as alkyl and aryl thiomethyl ethers and alkyl and aryl thioalkyl ethers,

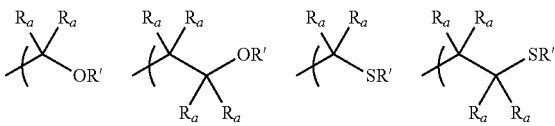

wherein each R$_a$ can be independently selected from hydrogen, alkyl and fluoro and R' can be selected from alkyl, cycloalkyl, aryl and arylalkyl.

Examples of alkoxy and aryloxy alkyl ethers include methoxymethyl ether, 2-methoxyethoxymethyl ether, benzyloxymethyl ether, p-methoxybenzyloxymethyl ether, 2-(trimethylsilyl)ethoxymethyl ether, 1-methoxyethyl ether, 1-ethoxyethyl ether, 1-n-propoxyethyl ether, 1-isopropoxyethyl ether, 1-n-butoxyethyl ether, 1-isobutoxyethyl ether, 1-sec-butoxyethyl ether, 1-tert-butoxyethyl ether, 1-ethoxy-n-propyl ether, methoxypropyl ether, ethoxypropyl ether, 1-methoxy-1-methylethyl ether, 1-ethoxy-1-methylethyl ether; tetrahydropyranyl (i.e. 2-tetrahydropyranyl) and related ethers.

Examples of alkyl and aryl thioalkyl ethers include methylthiomethyl ether, phenylthiomethyl ether, methylthioethyl ether and phenylthioethyl ether;

esters [—COR'], wherein R' can be selected from alkyl, cycloalkyl, aryl and arylalkyl. Examples of esters include acetyl, benzoyl, pivaloyl, methoxyacetyl, chloroacetyl, levulinyl ester;

carbamates [—CON(R)$_2$], wherein each R' can be independently selected from alkyl, cycloalkyl, aryl and arylalkyl; and carbonates [—COOR], wherein R' can be selected from alkyl, cycloalkyl, aryl and arylalkyl. Examples of carbonates include benzyl carbonate, p-nitrobenzyl carbonate, tert-butyl carbonate, 2,2,2-trichloroethyl carbonate, 2-(trimethylsilyl)ethyl carbonate, allyl carbonate.

As the skilled person knows, hydroxyl protecting groups are commonly named considering the oxygen atom. Thus, terms such as "ether", "ester" and "carbonate" when designating a hydroxyl protecting group really refer herein to the chemical group formed by the blocking group with the oxygen atom of the protected hydroxyl group.

The invention also provides "salts" of the compounds described in the present description. By way of illustration, said salts can be acid addition salts, base addition salts or metal salts, and can be synthesized from the parent compounds containing a basic or acid moiety by means of conventional chemical processes known by the persons skilled in the art. Such salts are generally prepared, for example, by reacting the free acid or base forms of said compounds with a stoichiometric amount of the suitable base or acid in water or in an organic solvent or in a mixture of the two. Non-aqueous media such as ether, ethyl acetate, ethanol, acetone, isopropanol or acetonitrile are generally preferred. Illustrative examples of said acid addition salts include inorganic acid addition salts such as, for example, hydrochloride, hydrobromide, hydroiodide, sulfate, nitrate, phosphate, etc., organic acid addition salts such as, for example, acetate, maleate, fumarate, citrate, oxalate, succinate, tartrate, malate, mandelate, methanesulfonate, p-toluenesulfonate, camphorsulfonate, etc. Illustrative examples of base addition salts include inorganic base salts such as, for example, ammonium salts and organic base salts such as, for example, ethylenediamine, ethanolamine, N,N-dialkylenethanolamine, triethanolamine, glutamine, amino acid basic salts, etc. Illustrative examples of metal salts include, for example, sodium, potassium, calcium, magnesium, aluminum and lithium salts.

Likewise, the compounds described in the present description can be obtained both as free compounds or as solvates (e.g., hydrates, alcoholates, etc.), both forms being included within the scope of the present invention. The solvation methods are generally known in the state of the art.

The term "pharmaceutically acceptable" relates to molecular entities and compositions being physiologically tolerable and normally not causing an allergic reaction or similar adverse reaction, such as gastric discomfort, dizziness and the like, when they are administered to a human being. Preferably, as used in this description, the term "pharmaceutically acceptable" means approved by a governmental regulatory agency or listed in the US pharmacopoeia or another generally recognized pharmacopoeia for use in animals, and more particularly in humans.

For those persons skilled in the art, it will be evident that the scope of the present invention also includes salts which are not pharmaceutically acceptable as possible means for obtaining pharmaceutically acceptable salts.

Unless otherwise indicated, the compounds of the invention also include compounds which differ in the presence of one or more isotopically enriched atoms. By way of illustration, compounds having the structures defined herein, with the exception of the substitution of at least one hydrogen by a deuterium or tritium, or the substitution of at least one carbon by a carbon enriched in $^{13}C$ or $^{14}C$, or at least one nitrogen by a nitrogen enriched in $^{15}N$, are within the scope of this invention.

As used herein, the term "about" means a slight variation of the value specified, preferably within 10 percent of the value specified. Nevertheless, the term "about" can mean a higher tolerance of variation depending on for instance the experimental technique used. Said variations of a specified value are understood by the skilled person and are within the context of the present invention. Further, to provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

In one aspect, the invention refers to a process for the preparation of Estetrol or a salt or solvate thereof, the process comprising
a) reacting a compound of formula (IV)

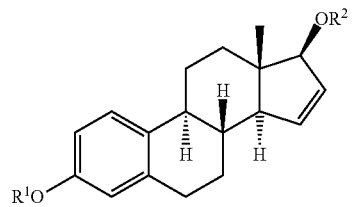

(IV)

or a salt or solvate thereof, wherein
$R^1$ is a hydroxyl protecting group selected from a silyl ether, an ether, an ester, a carbamate and a carbonate, and
$R^2$ is a hydroxyl protecting group selected from an ether,
with $OsO_4$ or a source of osmium tetroxide to produce Estetrol or a compound of formula (II) or a salt or solvate thereof

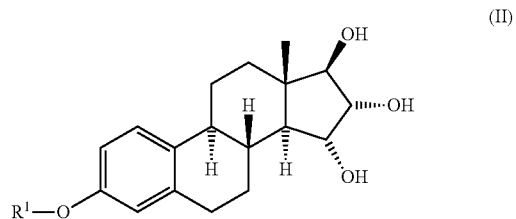

(II)

wherein $R^1$ is as defined previously; and
b) if a compound of formula (II) is obtained in step a), deprotecting said compound to produce Estetrol.

The oxidation of the compound of formula (IV) is carried out with an oxidizing agent providing selective cis-dihydroxylation of the carbon-carbon double bond to render Estetrol, said oxidizing agent being selected from $OsO_4$ or a source of osmium tetroxide such as potassium osmate(VI) dihydrate ($K_2OsO_4·2H_2O$) or osmium(III) chloride hydrate ($OsCl_3·xH_2O$) which easily oxidise to osmium(VIII). More preferably it is polymer-supported or immobilized $OsO_4$ (or a source of $OsO_4$) such as osmium tetroxide supported on poly(4-vinyl-pyridine) ($OsO_4$-PVP) (cf. G. Cainelli et al., Synthesis 1989, 45-47), AD-mix (alpha and beta), Os Encat™, Fibrecat™ microencapsulated osmium (VIII) oxide, osmium(VIII) oxide-pyridine PE fibres or dipotassium dioxotetrahydroxoosmate(VIII)-triethylamine PE fibres. In a particular embodiment, the amount of $OsO_4$ supported on PVP is about 5%. AD mix-α is a commercially available mixture containing $(DHQ)_2PHAL$ (hydroquinine 1,4-phthalazinediyl diether) 0.0016 mole, potassium carbonate, powder 0.4988 mole, potassium ferricyanide 0.4988 mole, and potassium osmate dihydrate 0.0007 mole. AD mix-β is a commercially available mixture containing $(DHQD)_2PHAL$ (hydroquinidine 1,4-phthalazinediyl diether) 0.0016 mole, potassium carbonate, powder 0.4988 mole, potassium ferricyanide 0.4988 mole, and potassium osmate dihydrate 0.0007 mole. Os Encat™ is $OsO_4$ immobilized in a polyurea matrix; in particular Os EnCat™ 40 has the following properties: Os metal content 4.8-5.7% w/w and $OsO_4$ loading 40-300 mmol/g (average 165 mmol/g). Fibrecat 3003™ is a commercially available osmium anchored homogeneous catalyst very similar to Encat™ 40.

In a preferred embodiment, an oxidation co-reagent or co-oxidant is added additionally, such as trimethylamine-N-oxide, triethylamine-N-oxide, dimethylbencilamine-N-oxide, N-methyl morpholine-N-oxide, Pyridine-N-oxide, TEMPO or hydrogen peroxide and derivatives, more preferably trimethylamine-N-oxide.

This reaction of cis-dihydroxylation is typically carried out in a suitable organic solvent, such as an ether, for example, an acyclic ether (e.g., diisopropylether, etc.) or a cyclic ether (e.g., tetrahydrofuran (THF), a dioxane, etc.), a halogenated solvent such as, for example, dichloromethane, etc., or in an aromatic solvent such as, for example, toluene, etc. Preferably, the solvent is THF. More preferably, $OsO_4$-PVP (poly(4-vinyl-pyridine)) and trimethylamine-N-oxide are used with THF as the solvent.

In a particular embodiment, the amount of the organic solvent may be a proportion between 3 and 20 mL per gram of the compound of formula (IV), more preferably between 8 and 15 mL per gram of the compound of formula (IV). Typically, the quantity of oxidation co-reagent may vary between 0.95 and 4 equivalents, more preferably between 1.0 and 2.5 equivalents and the amount of the oxidation reagent may be used between 10% and 50% per gram of the compound of formula (IV), more preferably between 15% and 25% per gram of the compound of formula (IV).

All the reagents may be added at room temperature, preferably under inert atmosphere, then the mixture is preferably heated such as at a temperature comprised between room temperature and 100° C. The reaction rate depends on the particular conditions including the temperature, where at a temperature comprised between 50° C. and 60° C. the reaction usually takes place in a time period of between 20-24 hours.

The product which would result from the cis-dihydroxylation (compound of formula (III)) is not isolated since the ether protecting group at position C17 is cleaved during reaction step a) or the subsequent isolation step leading directly to the C17 hydroxyl compound. Additionally, it has been found that in certain occasions the protecting group at position C3 of the compound of formula (IV) is also removed during reaction step a) or the subsequent isolation step directly giving rise to Estetrol. Accordingly, the oxidation reaction affords either a compound of formula (II), having the hydroxyl group at position C17 free, or directly Estetrol. See scheme 8 below:

formula (IV) is protected by a group other than an ether normally the cis-dihydroxylation provides a compound of formula (II), which has to be subsequently deprotected to afford Estetrol.

Estetrol can be prepared from a compound of formula (II) by conventional methods of deprotection known by persons skilled in the art Green and Wuts. in "Protective Groups in Organic Synthesis", 4th Edition (2007), Ed. John Wiley & Sons (ISBN 0-471-69754-0). The progress of the reaction of deprotection can be easily monitored by TLC.

For example, compounds of formula (II) wherein the hydroxyl group at C3 is protected by an ester, a carbonate or a carbamate can be easily converted into Estetrol by hydrolysis in basic or acid media according to well-established procedures of the state of the art.

Compounds of formula (II) wherein the hydroxyl group at C3 is protected by a silyl radical can be easily converted into Estetrol by the use of fluoride reagents such as fluoride salts or HF, acid media, oxidizing media, etc.

Compounds of formula (II) wherein the hydroxyl group at C3 is protected by an ether can be easily converted into Estetrol through hydrolysis in acid media (for example, for

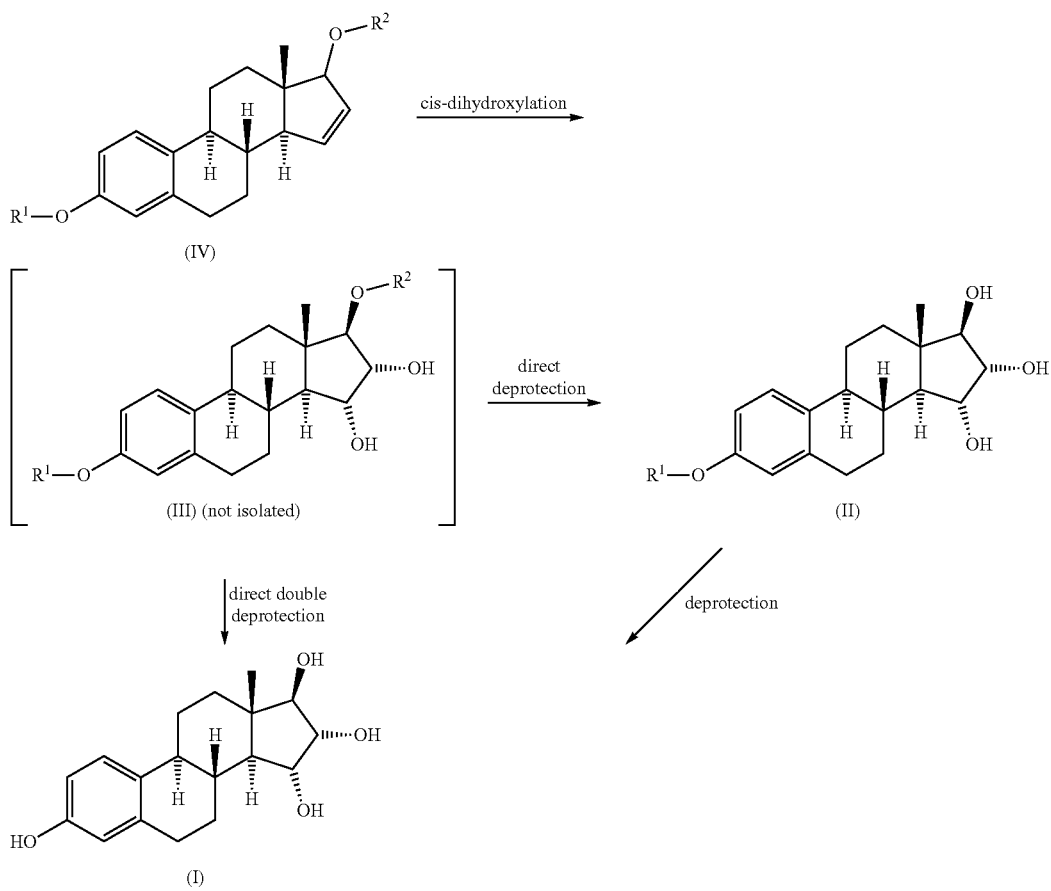

Scheme 8

According to one embodiment, Estetrol or a salt or solvate thereof is obtained by reaction of a compound of formula (IV) or a salt or solvate thereof with $OsO_4$ or a source of osmium tetroxide to produce a compound of formula (II) and deprotection of the compound of formula (II) to produce Estetrol. If the hydroxyl group at C3 in the compound of methyl ethers), hydrogenation (for example, for benzyl ethers), oxidation (for example, for aryl ethers), etc. In general, the deprotection reaction of ethers of formula (II) to afford Estetrol provides quantitative yields.

In a particular embodiment, the hydroxyl group at position C17 is protected by an alkoxy or aryloxy alkyl ether or an alkyl or aryl thioalkyl ether, preferably an alkoxy or aryloxy alkyl ether, more preferably an alkoxy alkyl ether.

In another embodiment, the hydroxyl group at position C17 is protected by an alkoxy or aryloxy alkyl ether or an alkyl or aryl thioalkyl ether of formula

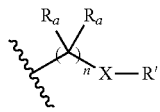

wherein X is O or S; n is 1 or 2; each $R_a$ is independently selected from hydrogen, alkyl and fluoro; and R' is selected from alkyl, cycloalkyl, aryl and arylalkyl. Preferably, n is 1; each $R_a$ is independently selected from hydrogen, and alkyl; and R' is an alkyl group. More preferably, X is O, n is 1, each $R_a$ is independently selected from hydrogen, and alkyl, and R' is an alkyl group, In a particular embodiment, the hydroxyl group at position C17 is protected by an alkoxy or aryloxy alkyl ether or an alkyl or aryl thioalkyl ether selected from (1-butoxyethyl) ether, tetrahydropyranyl (THP) ether, phenylthiomethyl (PTM) ether, and methoxymethyl (MOM) ether. More preferably, $R^2$ is 1-butoxyethyl, tetrahydropyranyl or methoxymethyl.

In a particular embodiment, the hydroxyl group at position C3 is protected by an ether, preferably an alkoxy or aryloxy alkyl ether or an alkyl or aryl thioalkyl ether, more preferably an alkoxy or aryloxy alkyl ether, even more preferably an alkoxy alkyl ether.

In another embodiment, the hydroxyl group at position C3 is protected by an alkoxy or aryloxy alkyl ether or an alkyl or aryl thioalkyl ether of formula

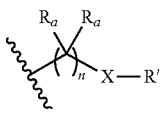

wherein X is O or S; n is 1 or 2; each $R_a$ is independently selected from hydrogen, alkyl and fluoro; and R' is selected from alkyl, cycloalkyl, aryl and arylalkyl. Preferably, n is 1; each $R_a$ is independently selected from hydrogen, and alkyl; and R' is an alkyl group. More preferably, X is O, n is 1, each $R_a$ is independently selected from hydrogen, and alkyl, and R' is an alkyl group, In a particular embodiment, the hydroxyl group at position C3 is protected by an alkoxy or aryloxy alkyl ether or an alkyl or aryl thioalkyl ether selected from (1-butoxyethyl) ether, tetrahydropyranyl (THP) ether, phenylthiomethyl (PTM) ether, and methoxymethyl (MOM) ether. Preferably, $R^1$ is 1-butoxyethyl, tetrahydropyranyl or methoxymethyl, more preferably $R^1$ is tetrahydropyranyl or methoxymethyl.

In another embodiment, the hydroxyl group at position C3 is protected by an ester, preferably selected from acetyl ester and benzoyl ester.

In a particular embodiment, the hydroxyl group at position C3 is protected by an ester, preferably selected from acetyl ester and benzoyl ester, and the hydroxyl group at position C17 is protected by an alkoxy or aryloxy alkyl ether or an alkyl or aryl thioalkyl ether as defined above, preferably by a group selected from (1-butoxyethyl)ether, tetrahydropyranyl (THP) ether, phenylthiomethyl (PTM) ether, and methoxymethyl (MOM) ether. More preferably, $R^1$ is benzoyl and $R^2$ is 1-butoxyethyl. This compound is designated herein as compound (IVa).

According to another embodiment, Estetrol or a salt or solvate thereof is directly obtained by reaction of a compound of formula (IV) or a salt or solvate thereof with $OsO_4$ or a source of osmium tetroxide. Preferably, direct double deprotection of the cis-dihydroxylation product takes place when the hydroxyl group at C3 in the compound of formula (IV) is protected by an ether or an ester, preferably an ether.

In a particular embodiment, both hydroxyl groups at positions C3 and C17 in the compound of formula (IV) are protected by an ether, which may be the same or different. Preferably, the hydroxyl groups at positions C3 and C17 are protected by an ether independently selected from an alkoxy or aryloxy alkyl ether or and alkyl or aryl thioalkyl ether as defined above, more preferably by a group independently selected from (1-butoxyethyl)ether, tetrahydropyranyl (THP) ether, phenylthiomethyl (PTM) ether, and methoxymethyl (MOM) ether. It is also preferred that both hydroxyl groups are protected by the same ether. More preferably, $R^1$ and $R^2$ are MOM groups [this compound is designated herein as compound (IVb)], or $R^1$ and $R^2$ are THP groups [this compound is designated herein as compound (IVc)].

In a particular embodiment, the 15β,16β-diol isomer is obtained in an amount equal to or lower than 3%, preferably equal to or lower than 2%, more preferably equal to or lower than 1.5%, with respect to the sum of 15β,16β-diol and 15α,16α-diol.

In a preferred embodiment, the compound of formula (IV) or a salt or solvate thereof is prepared from the free diol of formula (VI) (Δ-15-Estradiol) by introducing the corresponding protecting groups under conventional methods. If both hydroxyl groups are protected by the same group, the protection preferably occurs in one step; if the protecting groups are different, the hydroxyl group at position C3 is preferably protected first producing a compound of formula (V) and subsequently the hydroxyl group at position C17. See scheme 9.

Scheme 9

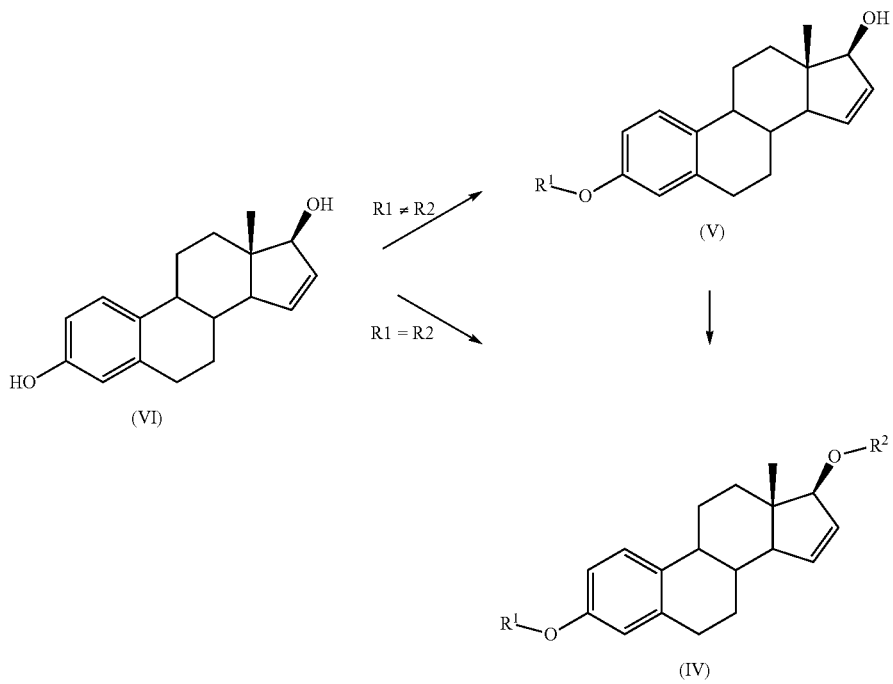

Thus, the compound of formula (IV) can be prepared from the compound of formula (VI) by conventional methods of protection known by persons skilled in the art Green and Wuts. in "Protective Groups in Organic Synthesis", 4th Edition (2007), Ed. John Wiley & Sons (ISBN 0-471-69754-0). The progress of the reactions of protection can be easily monitored by TLC.

According to a particular embodiment, the compound of formula (IVa) is prepared from the compound of formula (VI) by a process comprising protecting the hydroxyl group at C3 of the compound of formula (VI) as benzoyl ester to afford a compound of formula (Va) and then protecting the hydroxyl group at C17 as (1-butoxyethyl)ether. The 3-OH group of the compound of formula (VI) is preferably protected using benzoyl chloride in dichloromethane and triethylamine as base and the 17-OH group of the compound of formula (Va) is preferably protected using butylvinyl ether in THF in the presence of p-toluenesulphonic acid.

According to a particular embodiment, the compound of formula (IVb) is prepared from the compound of formula (VI) by a process comprising simultaneously protecting both hydroxyl groups at positions C3 and O17 as MOM ethers. This double protection can be achieved for instance using formaldehyde dimethyl acetal in THF in the presence of lithium bromide and p-toluenesulphonic acid or using bromomethyl methyl or chloromethyl methyl ether in a solvent selected from dichloromethane, THF, Toluene, MeTHF and DMAc, in the presence of diisopropylethylamine or using formaldehyde dimethyl acetal in dichloromethane in the presence of phosphorus pentoxide.

According to a particular embodiment, the compound of formula (IVc) is prepared from the compound of formula (VI) by a process comprising simultaneously protecting both hydroxyl groups at positions C3 and C17 as THP ethers. This double protection can be achieved for instance using 3,4-dihydro-2H-pyran in dichloromethane in the presence of p-toluenesulphonic acid.

In a preferred embodiment, the invention refers to a process for the preparation of Estetrol or a salt or solvate thereof, the process comprising protecting a compound of formula (VI)

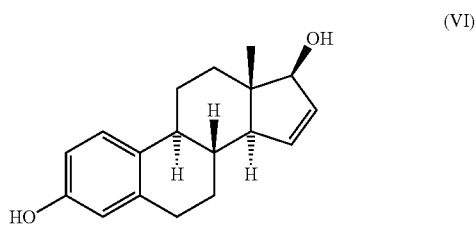

or a salt or solvate thereof, to produce a compound of formula (IV)

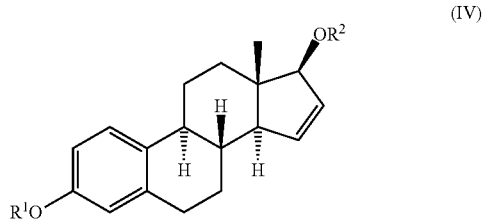

or a salt or solvate thereof, wherein $R^1$ and $R^2$ are ether hydroxyl protecting groups, which may be the same or different; and reacting the compound of formula (IV) or a salt or solvate thereof with $OsO_4$ or a source of osmium tetroxide to produce Estetrol.

Preferably, the hydroxyl groups at positions C3 and C17 according to the preferred embodiment above are protected by an ether independently selected from an alkoxy or aryloxy alkyl ether or an alkyl or aryl thioalkyl ether as defined above, more preferably by a group independently selected from (1-butoxyethyl)ether, tetrahydropyranyl (THP) ether, phenylthiomethyl (PTM) ether, and methoxymethyl (MOM) ether. It is also preferred that both hydroxyl groups are protected by the same ether. More preferably, $R^1$ and $R^2$ are MOM groups [compound (IVb)] or $R^1$ and $R^2$ are THP groups [compound (IVc)].

Thus, according to a preferred embodiment in one synthetic step both hydroxyl groups at positions C3 and C17 of the compound of formula (VI) may be protected simultaneously as ethers to afford a compound of formula (IV), and then, cis-dihydroxylation of said compound of formula (IV) is accompanied by the double deprotection directly affording Estetrol. This process is specially useful from an industrial point of view since the overall yield of these two synthetic steps is practically 100% molar and the ratio between the 15α,16α-diol and 15β,16β-diol is 99/1.

The preparation of the compound of formula (VI) is well known in the state of the art (see for instance, Cantrall et al., J. Org. Chem. 1964, 29, 214-217; Johnson et al., J. Am. Chem. Soc. 1957, 79, 2005-2009; Poirier et al., Tetrahedron 1991, 47, 7751-7766; Nambara et al., Steroids 1976, 27, 111-121; Li et al.; Steroids 2010, 75, 859-869). According to a particular embodiment, the compound of formula (VI) is prepared following the scheme depicted below in Scheme 10:

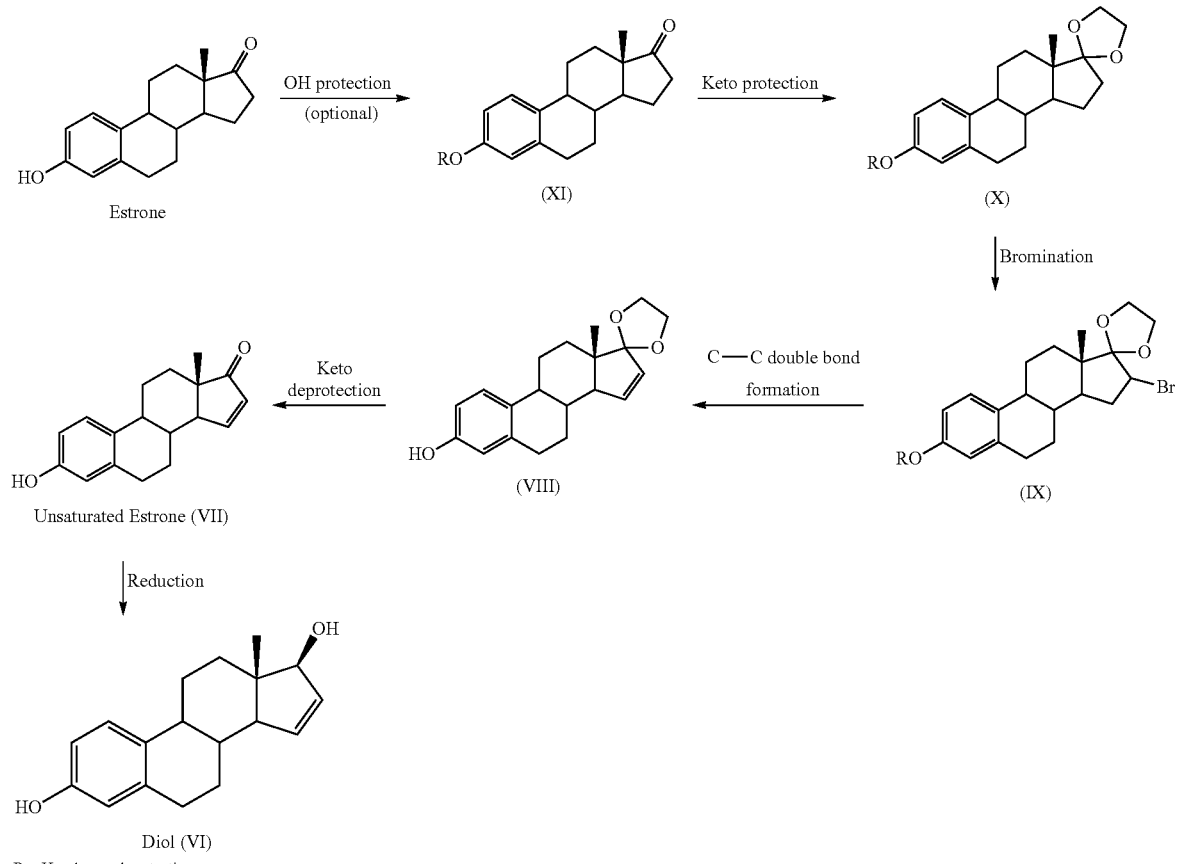

The 3-OH group of the estrone is optionally protected for instance by acylation, silylation, formation of an ether, etc. In the case of the acylation, the 3-OH group is preferably acylated using a reagent selected from benzoyl, benzyl or acetyl chloride in dichloromethane and triethylamine as base.

Then, the carbonyl group of intermediate product (XI) may be protected by treatment with ethylene glycol, triethylortoformiate and p-toluene sulfonic acid to render compound (X) in practically quantitative yield.

Subsequently, an alpha-bromination may be carried out with pyridinium bromide in THF in presence of ethylene glycol to obtain the compound (IX). In a particular embodiment, the amount of ethylene glycol may be from 5 to 25% with respect to the amount of THF.

The carbon-carbon double bond of ring D may be achieved with treatment of the compound (IX) with t-BuOK in DMSO; under said conditions, if an ester is used as hydroxyl protecting group at C3, it is unstable.

In a particular embodiment, the dehydrobromination reaction is carried out using between 1 and 10, more preferably between 2 and 6 equivalents of t-BuOK per equivalent of compound of formula (IX) and the amount of DMSO may be between 5 and 20 mL per gram of the compound of formula (IX), more preferably between 7 and 11 mL per gram of the compound of formula (IX).

In a preferred embodiment the dehydrobromination reaction is carried out using between 2 and 6 equivalents of t-BuOK equivalent of compound of formula (IX) and an amount of DMSO between 7 and 11 mL per gram of the compound of formula (IX), The compound of formula (VIII) may be prepared from the compound of formula (X) in a one-pot process, without isolating the intermediate compound (IX). However, in a preferred variant of the invention, the compound of formula (IX) is isolated.

The compound of formula (VIII) obtained in the dehydrobromination reaction does not need further purifications (such as crystallizations or chromatographies) nor requires to be dried. Thus, the dioxolane group of compound (VIII), without purification or drying, may be hydrolyzed by using p-toluene sulfonic acid to obtain unsaturated estrone (VII) in practically quantitative yield.

The conversion of unsaturated estrone (VII) into the diol (VI) can be carried out by means of any reduction reaction which allows the transformation of the keto group at C17 of a compound of formula (VII) into a hydroxyl group to render a compound of formula (VI). Thus, the reduction reaction can be carried out under conventional conditions known in the art. In a particular embodiment, the reaction is performed using a reducing agent selected from a metallic hydride such as sodium borohydride, sodium cyanoborohydride, potassium borohydride, potassium cyanobohydride and lithium aluminum hydride. In a preferred embodiment, the reducing agent is sodium borohydride, preferably in the presence of cerium trichloride (NaBH$_4$/CeCl$_3$). More preferably, the reducing agent for use herein is NaBH$_4$ in combination with CeCl$_3$ hydrate, preferably cerium trichloride heptahydrate (CeCl$_3$.7H$_2$O).

In a particular embodiment, the reduction reaction is carried out using between 1 and 10, preferably between 1 and 5, more preferably between 1 and 3 equivalents of the reducing agent per equivalent of compound of formula (VII), or a salt or solvate thereof.

In a preferred embodiment, the reaction of the compound of formula (VII) with the reducing agent is carried out in a mixture of a protic solvent, such as MeOH and THF. In particular, it is preferred to suspend the compound of formula (VII) and the reducing agent in a mixture of a protic solvent, preferably MeOH and THF, at 0° C.-5° C. and to stir the mixture at said low temperature. A preferred volume ratio of MeOH to THF is 2:1 to 5:1.

The preparation of the diol (VI) is not limited to the specific process shown in Scheme 10, but as the skilled person will appreciate, protection and deprotection of the hydroxyl group at position 3 and the keto group at position 17 can be performed at any stage of the synthesis. The most suitable stage for said protection and/or deprotection can be readily determined by those skilled in the art.

The process depicted in Scheme 10 can provide the intermediate diol (VI) in a high purity (typically above 98%) and yield (80% overall yield from the starting estrone to the isolation of the diol (VI)).

In additional preferred embodiments, the preferences described above for the processes are combined. The present invention is also directed to such combinations of preferred conditions of the processes.

In another aspect, the present invention refers to a compound of formula (IV)

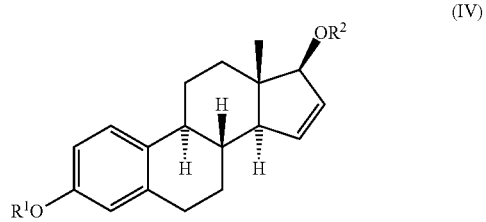

(IV)

or a salt or solvate thereof, wherein
R$^1$ and R$^2$ are as defined herein, with the proviso that when R$^1$ is methyl then R$^2$ is not a 2-propynyl group nor a 2-tetrahydropyranyl group.

In a particular embodiment, R$^2$ is an alkoxy or aryloxy alkyl ether or an alkyl or aryl thioalkyl ether.

Preferably, R$^2$ is a group of formula

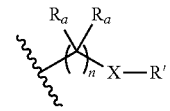

wherein X is O or S; n is 1 or 2; each R$_a$ is independently selected from hydrogen, alkyl and fluoro; and R' is selected from alkyl, cycloalkyl, aryl and arylalkyl. Preferably, n is 1; each R$_a$ is independently selected from hydrogen, and alkyl; and R' is an alkyl group. More preferably, X is O, n is 1, each R$_a$ is independently selected from hydrogen, and alkyl, and R' is an alkyl group, In a particular embodiment, R$^2$ is selected from (1-butoxyethyl)ether, tetrahydropyranyl (THP) ether, phenylthiomethyl (PTM) ether, and methoxymethyl (MOM) ether. More preferably, R$^2$ is 1-butoxyethyl, tetrahydropyranyl or methoxymethyl.

In a particular embodiment, R$^1$ is an ester, preferably an acetyl ester or a benzoyl ester; or an ether, preferably an alkoxy or aryloxy alkyl ether or an alkyl or aryl thioalkyl ether.

In another embodiment, R$^1$ is an ester, preferably an acetyl ester or a benzoyl ester; or an ether of formula

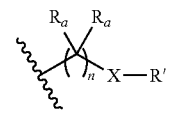

wherein X is O or S; n is 1 or 2; each R$_a$ is independently selected from hydrogen, alkyl and fluoro; and R' is selected from alkyl, cycloalkyl, aryl and arylalkyl; more preferably, n is 1; each R$_a$ is independently selected from hydrogen, and alkyl; and R' is an alkyl group; even more preferably, X is O, n is 1, each R$_a$ is independently selected from hydrogen, and alkyl, and R' is an alkyl group, In a particular embodiment, R$^1$ is selected from acetyl ester, benzoyl ester, (1-butoxyethyl)ether, tetrahydropyranyl (THP) ether, phenylthiomethyl (PTM) ether, and methoxymethyl (MOM) ether. More preferably, R$^2$ is benzoyl ester, tetrahydropyranyl or methoxymethyl.

In a particular embodiment, the compound of formula (IV) is selected from

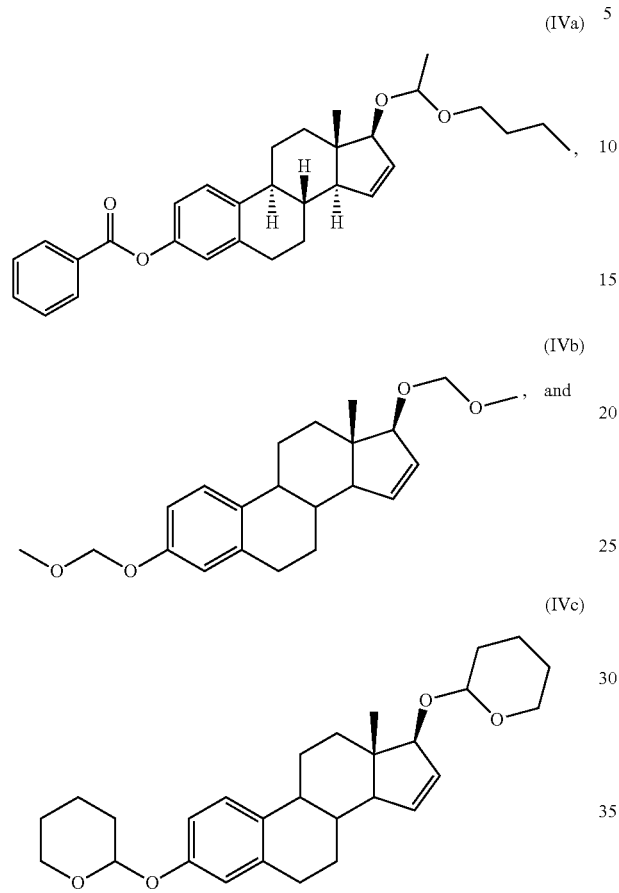

or a salt or solvate thereof.

The following examples illustrate the invention and must not be considered in a limiting sense thereof.

EXAMPLES

Comparative Example 1

Preparation of Estetrol according to Example 1 of WO2013/050553

Step 1: estra-1,3,5(10),15-tetraene-3,17β-diol bis(dimethyl-tert-butylsilyl)ether

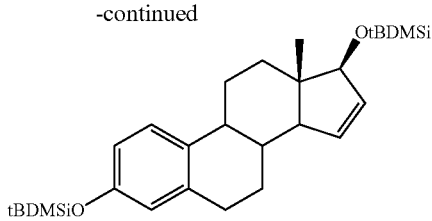

To a solution of 3-t-butyldimethylsiloxy-estra-1,3,5(10)-15-tetraene-17-ol (5 g) in 50 ml of dimethylformamide were added imidazole (6.8 g) and dimethyl-tert-butylsilyl-chloride (3.0 eq.) and allowed to stand at room temperature until completion of the reaction. Water 100 ml and AcOEt 100 ml were added. The two phases were separated, the aqueous phase was extracted with AcOEt 100 ml. The resulting solution was evaporated. The residue was crystallized from methanol to afford (6.9 g) of estra-1,3,5(10),15-tetraene-3,17-diol bis(dimethyl-tert-butylsilyl)ether.

Step 2: estra-1,3,5(10),15α,16α,17β-tetrol

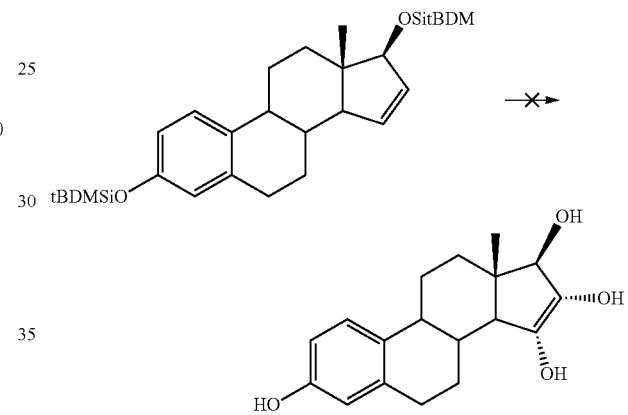

To a stirred solution of estra-1,3,5(10),15-tetraene-3,17β-diol bis(dimethyl-tert-butylsilyl)ether (5 g) and formic acid (1.15 ml) in acetone (50 ml) at 0° C. was added gradually a solution of potassium permanganate (1.57 g) in water (10 ml) and acetone (50 ml). No completion of the reaction was obtained; the reaction was quenched with a 10% aqueous solution of KHSO₃. Acetone was partially removed. The precipitate was collected by filtration to afford 95% of the staring material estra-1,3,5(10),15-tetraene-3,17β-diol bis(dimethyl-tert-butylsilyl)ether and 1-2% of estra-1,3,5(10),15β,16β,17β-tetrol.

Comparative Example 2

Preparation of Estetrol according to Example 2 of WO2013/050553

Step 1

-continued

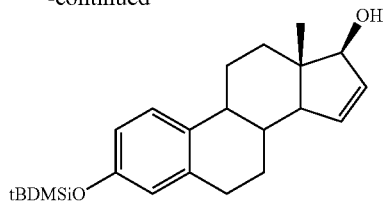

To a solution of estra-1,3,5(10)-15-tetraene-3,17-diol (4 g) in 40 ml of dimethylformamide were added imidazole (5.4 g) and dimethyl-tert-butylsilyl-chloride (1.1 eq.) and allowed to stand at room temperature until completion of the reaction. Water 80 ml and AcOEt 80 ml were added. The two phases were separated; the aqueous phase was extracted with AcOEt 80 ml. The resulting solution was evaporated. The residue was crystallized from methanol to afford (5.4 g) of 3-t-butyldimethylsiloxy-estra-1,3,5(10),15-tetraene-17-diol.

Step 2. WO2013/050553 Example 2

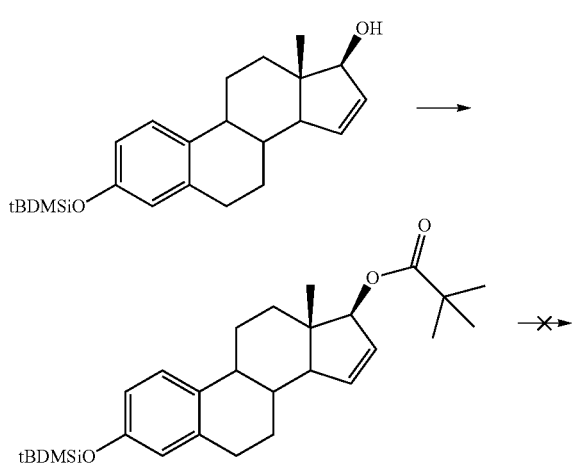

To a solution of 3-t-butyldimethylsiloxy-estra-1,3,5(10)-15-tetraene-17-ol (5 g) in 50 ml of dichloromethane and 1.8 ml of triethylamine were added drop wise 1.75 g of pivaloyl chloride in 8 ml methylene chloride and allowed to stand at 0° C. until completion of the reaction. Then the solution was stirred at room temperature for 1 hour. Water 30 ml was added. The two phases were separated; the organic phase was washed twice with 100 ml of water. The resulting solution was precipitated with Heptane and the solid product was filtered off.

Then estra-1,3,5(10),15-tetraene-3-dimethyl-tert-butylsilyl,17-pivaloyl-diol (4 g) and formic acid (0.95 ml) were solved in acetone (40 ml) at 0° C. A solution of potassium permanganate (1.25 g) in water (8 ml) and acetone (40 ml) was added slowly. No completion of the reaction was obtained. The reaction was quenched with a 10% aqueous solution of KHSO₃. Acetone was partially removed then the precipitate was collected by filtration to afford 95% of estra-1,3,5(10),15-tetraene-3-dimethyl-tert-butylsilyl,17-pivaloyl-diol and 2-3% of estra-1,3,5(10),15β,16β,17β-tetrol.

Comparative Example 3

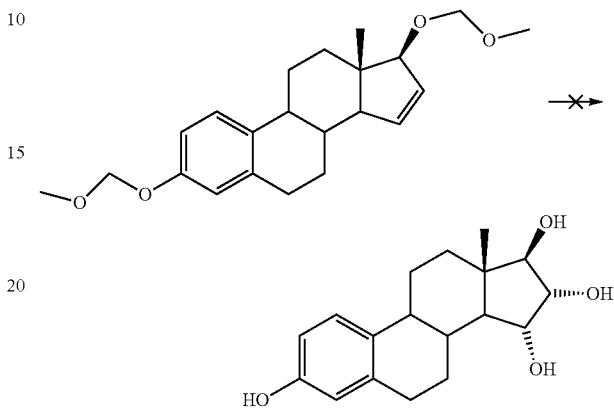

To a stirred solution of 3,17-methoxy methyl ether-3,17β-dihydroxy-Δ-15-estradiol (0.17 g) and formic acid (0.04 ml) in acetone (1.7 ml) at 0° C. was added gradually a solution of potassium permanganate (53 mg) in water (0.35 ml) and acetone (1.7 ml). No completion of the reaction was obtained; the reaction was quenched with a 10% aqueous solution of KHSO₃. Acetone was partially removed. The precipitate was collected by filtration to afford 88% of the staring material 3,17-methoxy methyl ether-3,17β-dihydroxy-Δ-15-estradiol and 9% of estra-1,3,5(10),15β,16β,17β-tetrol.

Example 1

Preparation of Estrone-3-benzoate

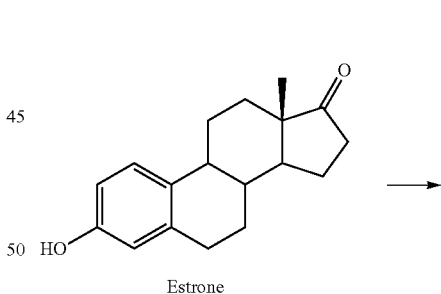

Estrone

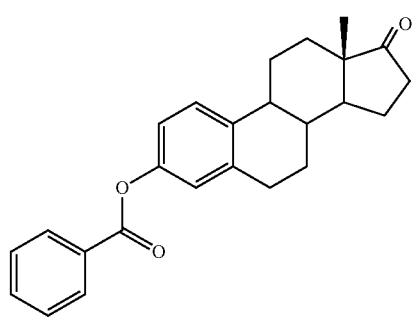

To 150 g of Estrone in 1500 mL of dichloromethane and 154 mL of triethylamine (d: 0.725 g/mL), 77.2 ml of benzoyl chloride were added at a temperature below 30° C.

After the addition, it was stirred at 20±5° C. until positive control by TLC. Then, 600 mL of a solution of 10% VN HCl was added, it was stirred and the two phases were separated. The aqueous phase was extracted with two aliquots of 300 mL of dichloromethane. The final organic phase was treated with 450 mL of 10% WN of sodium bicarbonate and was extracted again with an aliquot of 300 mL of dichloromethane. The resulting organic phase was treated with 450 mL of water. This aqueous phase was also extracted with an aliquot of 300 mL of dichloromethane. The final organic phase was concentrated under vacuum until a final volume of 450 mL. The solvent was changed with methanol by subsequent steps of addition and evaporation with three portions of 450 mL of methanol, concentrating in each case until a final volume of 450 mL. The final suspension was stirred at 0/5° C. for 30 minutes and then, the solid was filtered off. The solid was washed with 150 mL of methanol at 0/5° C. and it was dried at 50° C., to afford a final dry cake: 207.5 g of Estrone-3-benzoate. Yield: 100% Molar.

Example 2

Preparation of 17,17-ethylenedioxy-Estrone-3-benzoate

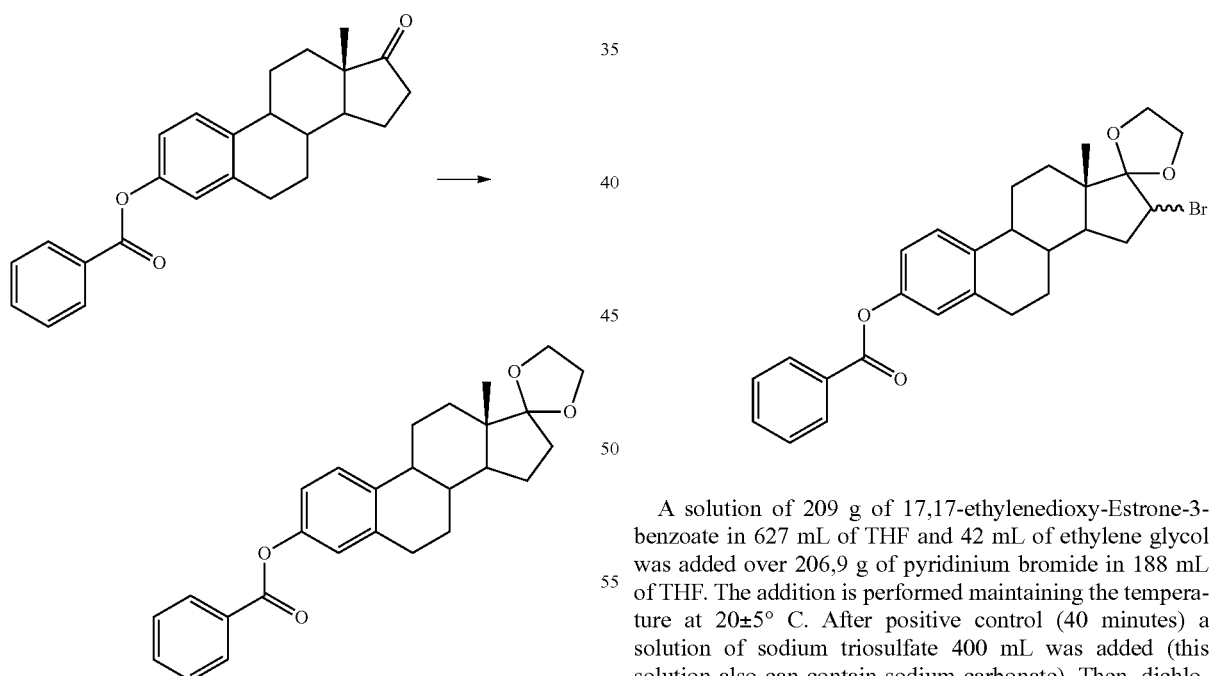

207.5 g of starting material Estrone-3-benzoate were suspended in 415 mL of ethylene glycol and 207 mL of triethylortoformiate and 4.25 g of p-toluenesulfonic acid were added. It was stirred at 35±5° C. until positive control (about 15 hours). Then, 7.5 mL of pyridine were added at room temperature, and after stirring for 15 minutes, 2900 mL of water were added over the mixture. The suspension was stirred at room temperature for 30 minutes and filtered. It was washed with 620 mL of water and dried at 50° C. Final dry cake: 229.0 g of 17,17-ethylenedioxy-Estrone-3-benzoate. Yield: 99% Molar Example 3

Preparation of 16-bromo-17,17-ethylenedioxy-Estrone-3-benzoate

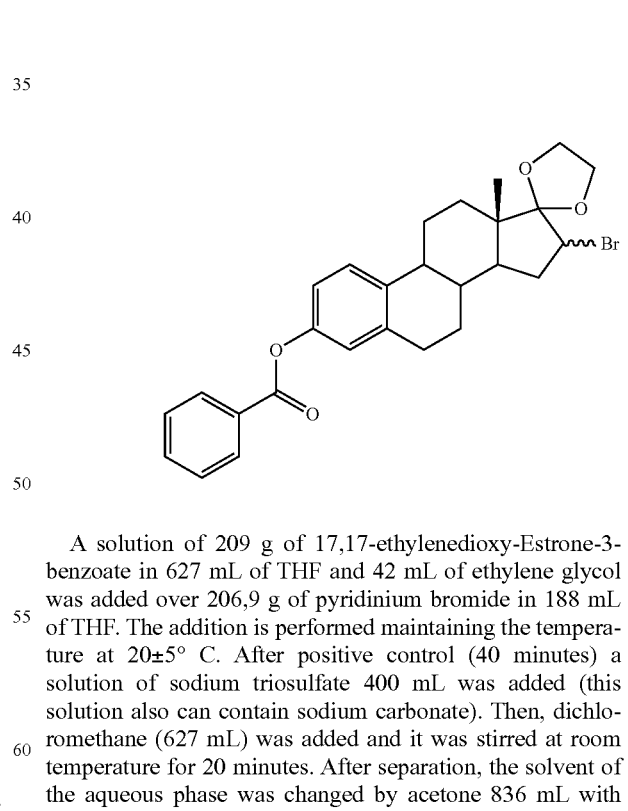

A solution of 209 g of 17,17-ethylenedioxy-Estrone-3-benzoate in 627 mL of THF and 42 mL of ethylene glycol was added over 206,9 g of pyridinium bromide in 188 mL of THF. The addition is performed maintaining the temperature at 20±5° C. After positive control (40 minutes) a solution of sodium triosulfate 400 mL was added (this solution also can contain sodium carbonate). Then, dichloromethane (627 mL) was added and it was stirred at room temperature for 20 minutes. After separation, the solvent of the aqueous phase was changed by acetone 836 mL with distillations and charges of acetone, obtaining a final suspension of 400 mL. It was stirred at 0/5° C. for 1 hour and filtered. It was washed with 100 mL of acetone and it was dried at 50° C. Final dry cake: 218.6 g of 16-bromo-17,17-ethylenedioxy-Estrone-3-benzoate. Yield: 99% Molar.

Example 4

Preparation of Δ-15-17,17-ethylenedioxy-Estrone

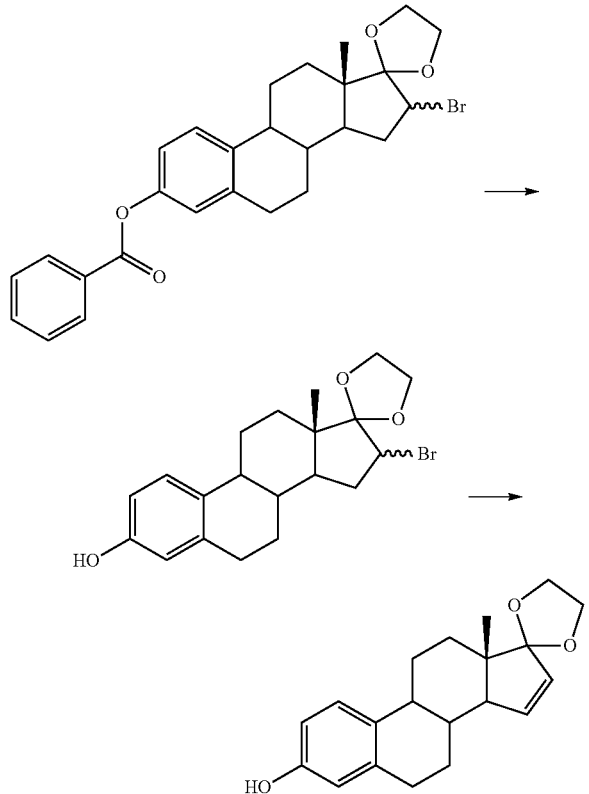

Over 200 g of 16-bromo-17,17-ethylenedioxy-Estrone-3-benzoate in 2000 mL of DMSO, 300 g of potassium t-butoxide were added. The mixture was heated at 40/45° C. for 20 hour. After positive control, the mixture was precipitated over water (1000 mL) and the pH was adjusted with an aqueous solution of 10% sulphuric acid, to obtain a pH 7/8. The resulting suspension was filtered and washed with water (200 mL) to afford 13.5 g of Δ-15-17,17-ethylenedioxy-Estrone as a wet cake.

The cake was drained and used as such in the next step.

Example 5

Preparation of Δ-15-Estrone

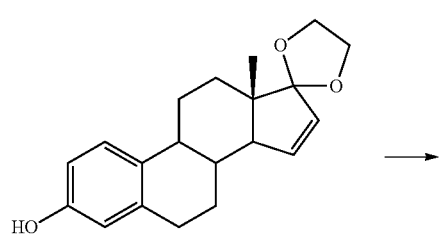

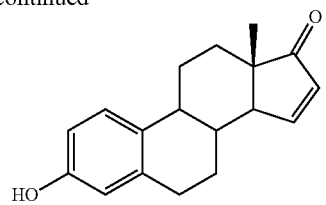

The wet cake of the previous step Δ-15-17,17-ethylenedioxy-Estrone was suspended again in 750 mL of acetone and 4.5 g of p-toluenesulfonic acid were added (if pH is not below 3, more p-TSA is added). The reaction was complete after 1 hour at 20±5° C., and then 3 mL of pyridine was charged. The mixture was concentrated until 300 mL and 300 mL of water were added. It was filtered and washed with 150 mL of water.

The cake was drained and dried at 50° C. Final dry cake: 107.9 g. Yield: 100% Molar.

Example 6

Preparation of Δ-15-Estradiol

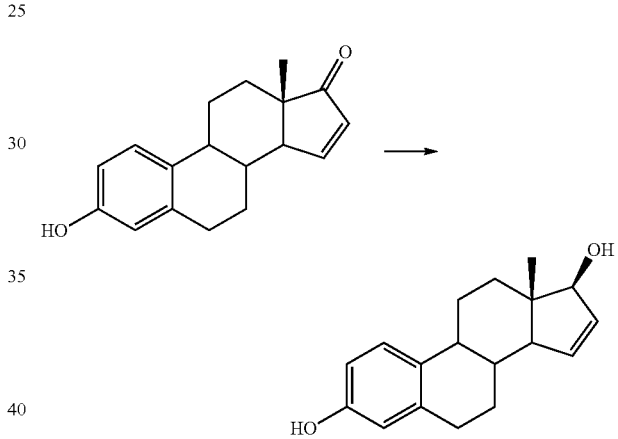

Over 32.5 g of Δ-15-Estrone in 114 mL of THF, 488 mL of methanol and 9.75 g of cerium trichloride heptahydrate, 1.4 g of sodium borohydride were added portion-wise at 0/5° C. The reaction was complete in 10 minutes. Then 100 mL of water were added, it was concentrated under vacuum until 100 mL and 50 mL more of water are added. It was stirred at 5/10° C. for 1 hour, filtered and washed with 120 mL of water. The cake was drained and resuspended in methanol, filtered and dried at 50° C. The final amount of dry cake is 30.5 g. Yield: 93% Molar.

Example 7

Preparation of Δ-15-estradiol-3-benzoate

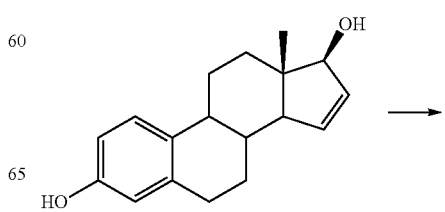

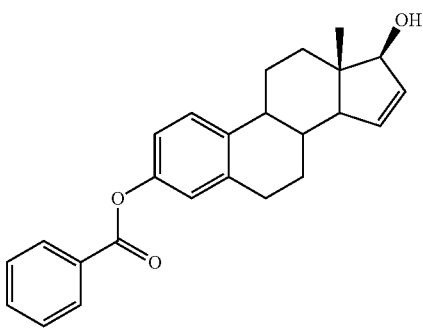

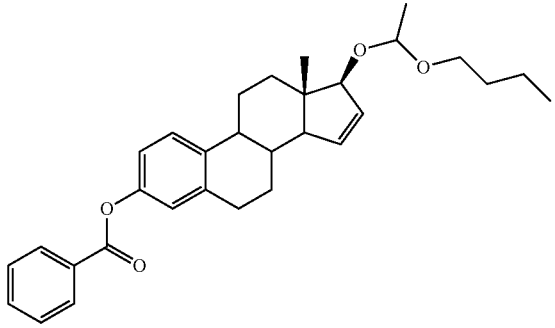

Δ-15-estradiol (10 g) was dissolved in 100 ml of dichloromethane and 11 ml of triethylamine under inert atmosphere, at a temperature of about 10-15° C. and 5.15 ml of Benzoyl chloride were added thereto at a temperature lower than 30° C. The reaction mixture was stirred at room temperature for about one hour until completion of the reaction was observed by HPLC.

A 5% aqueous solution of hydrochloric acid (40 ml) was added at room temperature. The resulting mixture was kept until complete separation of the two phases. The aqueous phase was extracted twice with dichlormethane (20 ml×2) and all the organic phases were mixed and washed with a 5% aqueous solution of NaHCO3 (30 ml) and water (30 ml). After decantation, the aqueous phase is extracted with dichloromethane (20 ml). Then, the organic phases were mixed and evaporated under reduced pressure and ethyl acetate was added (30 ml×3 times) and evaporated under reduced pressure. Heptane (60 ml) was added slowly to afford a suspension. The suspended solid was filtered and washed with heptane and dried in an oven at 50° C. to yield 11.59 g.

Example 8

Preparation of 17-(1-butoxyethyl)ether-3,17β-dihydroxy-Δ-15-estradiol-3-benzoate Δ-15-estradiol-3-benzoate (5.5 g) was dissolved in 16 ml of THF and molecular sieves (1.1 g) and 2.85 ml of butylvinyl ether were added under inert atmosphere at room temperature. Then p-toluenesulphonic acid (0.03 g) was added. The reaction mixture was stirred at room temperature until completion of the reaction was observed by HPLC. Then pyridine (0.01 ml) was added and the resulting mixture was filtered off and washed with THF (5.5 ml). The resulting organic phase was washed with an aqueous solution of NaCl 10% (35 ml) and evaporated under vacuum to afford 27 mL.

The liquid phase was used in the next step without further purification. Estimated yield 6.9 g of 17-(1-butoxyethyl) ether-3,17β-dihydroxy-Δ-15-estradiol-3-benzoate.

NMR-H$^1$: 8.08 (2H); 7.71 (1H); 7.56 (2H); 7.30 (1H); 6.98 (1H); 6.93 (1H); 6.03 (1H); 5.72 (1H); 4.74 (1H); 4.26 (1H); 3.56-3.33 (2H); 2.83 (2H); 2.33-1.89 (3H); 1.55-1.26 (4H); 1.21 (3H), 0.84(3H); 0.77 (3H).

NMR-C$^{13}$: 164.6; 148.3; 137.8; 137.7; 137.5; 133.9; 133.2; 130.9; 129.6; 129.0; 128.9; 126.1; 121.5; 118.8; 98.9; 88.1; 87.1; 64.1; 55.9; 54.8; 50.8; 43.9; 39.9; 35.4; 31.4; 30.3; 28.7; 26.7; 25.5; 20.5; 19.7; 18.9; 13.6; 12.9.

Example 9

Preparation of 15α,16α,17β-trihydroxy-estradiol 3-benzoate ester

Over the solution of example 8 containing 17β-1-butoxyethyl ether-hydroxy-Δ-15-estradiol 3-benzoate ester (6.9 g) in 37 ml of THF trimethylamine N-oxide (3.5 g) were added at room temperature. PVP-OsO4 (1.7 g) and THF (9 ml) were added at room temperature, the mixture was heated until 50-55° C. for 20-24 h. Then, the mixture was cooled down and the organic layer was washed with a solution of p-TsOH in water, then filtered off and the solid was extracted with THF.

The liquid phase (65 mL) was used in the next step without further purification.

Estimated yield 5.8 g (98% molar) of 15α,16α,17β-trihydroxy-estradiol 3-benzoate ester.

Example 10

Preparation of Estetrol

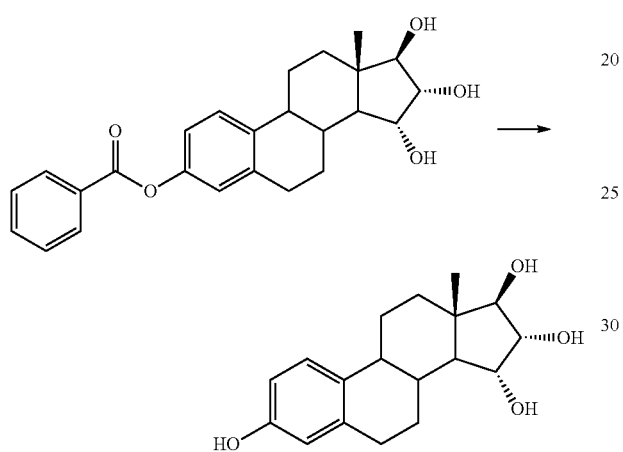

Over the solution of example 9 containing 15α,16α,17β-trihydroxy-estradiol 3-benzoate ester (5.8 g) MeOH (80 mL) were added and evaporated under vacuum (30 mL).

3 g of NaOH were added. The mixture was heated at 40/45° C. for 2 hour. After positive control, the mixture was precipitated over water (90 mL) and the pH was adjusted with an aqueous solution of 10% hydrochloric acid, to obtain a pH 7/8. The resulting suspension was filtered and washed with water (60 mL).

The wet cake was dried in an oven at 50° C. to yield 4.1 g (94% molar) of Estetrol (I).

The ratio between the α-15,16-diol and β-15,16-diol is 99/1.

Example 11

Preparation of Estetrol (I)

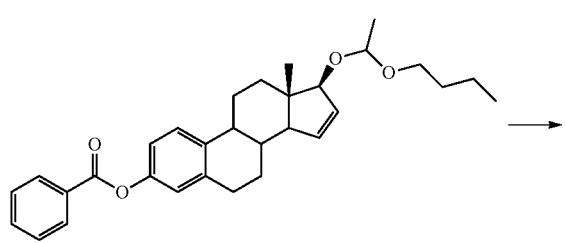

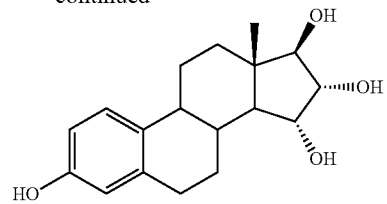

Over the solution of example 8 containing 1713-1-butoxyethyl ether-hydroxy-Δ-15-estradiol 3-benzoate ester (6.9 g) in 37 ml of THF, trimethylamine N-oxide (3.5 g) was added at room temperature. PVP-OsO4 (1.7 g) and THF (9 ml) were added at room temperature, the mixture was heated to 50-55° C. for 20-24 h. Then, the mixture was cooled down and the organic layer was washed with a solution of K$_2$CO$_3$ in water, then filtered off and the solid was extracted with THF.

The wet cake was dried in an oven at 50° C. to yield 4.0 g (91.7% molar) of Estetrol (I).

The ratio between the α-15,16-diol and β-15,16-diol is 98/2.

Example 12

Preparation of 3,17-methoxy methyl ether-3,17β-dihydroxy-Δ-15-estradiol

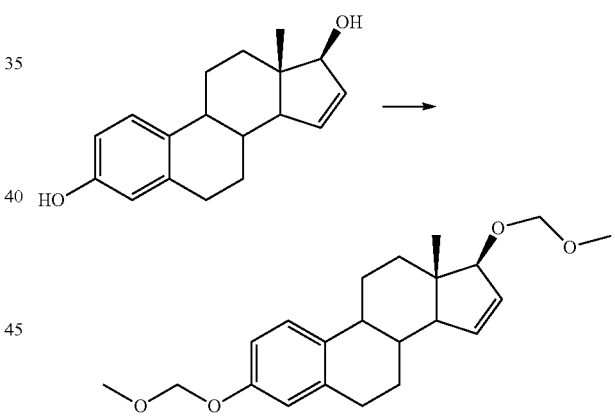

3-17β-dihydroxy-Δ-15-estradiol (0.5 g) was dissolved in 5 ml of THF, Lithium bromide 0.9 g and 0.4 ml of formaldehyde dimethyl acetal were added under inert atmosphere at room temperature. Then p-toluenesulphonic acid (0.025 g) was added. The reaction mixture was stirred at room temperature until completion of the reaction was observed by HPLC. The resulting mixture was washed with an aqueous solution of HCl and water until pH 7. The organic phase was concentrated by evaporation under vacuum and chromatographed on silica gel.

0.42 g of 3,17-methoxy methyl ether-3,17β-dihydroxy-Δ-15-estradiol were collected.

NMR-H$^1$: 7.15 (1H); 6.76 (1H); 6.71 (1H); 6.05 (1H); 5.76 (1H); 5.13 (2H, OCH$_2$O); 4.65 (2H, OCH$_2$O); 4.18 (1H); 3.48 (OCH$_3$); 3.29 (OCH$_3$); 2.83 (2H); 2.29-2.17 (2H); 2.07-1.89 (3H); 1.75-1.68 (2H); 1.51-1.34 (4H); 0.80 (3H).

NMR-C$^{13}$: 154.6; 137.3; 133.1; 131.2; 125.9; 115.9; 113.6; 95.7; 93.7; 90.1; 67.0; 55.9; 55.3; 54.6; 50.5; 44.1; 35.6; 34.4; 28.9; 26.9; 25.6; 25.1; 12.9.

Example 13

Preparation of 3,17-methoxy methyl ether-3,17β-dihydroxy-Δ-15-estradiol

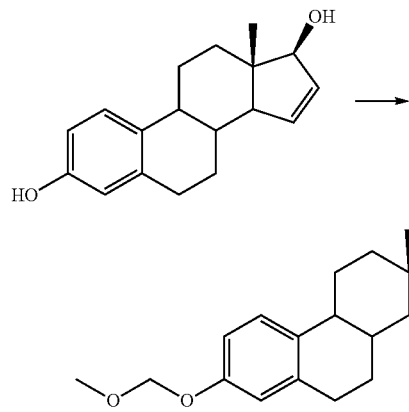

3-17β-dihydroxy-Δ-15-estradiol (0.2 g) was dissolved in 4 ml of CH$_2$Cl$_2$, Diisopropilethylamine 0.38 ml and 0.2 ml of chloromethyl methyl ether was added in two portions under inert atmosphere at room temperature. The reaction mixture was stirred at room temperature until completion of the reaction was observed by HPLC. The resulting mixture was washed with an aqueous solution of HCl and water until pH 7. The organic phase was concentrated and used in the next step without further purification I.

Estimated product 3,17-methoxy methyl ether-3,17β-dihydroxy-Δ-15-estradiol 0.17 g.

Example 14

Preparation of Estetrol (I)

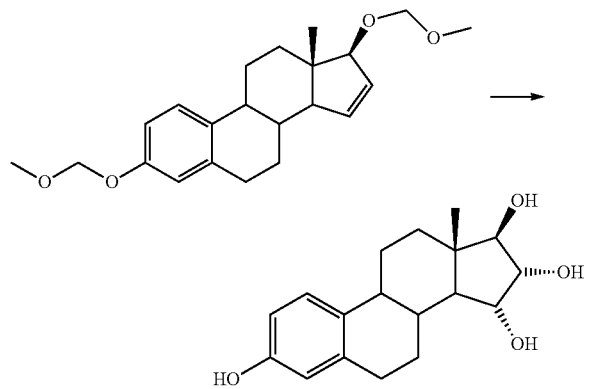

To a stirred solution of 3,17-methoxy methyl ether-3,17β-dihydroxy-Δ-15-estradiol (0.3 g) and THF (2.0 ml), trimethylamine N-oxide (0.15 g) were added at room temperature. PVP-OsO4 1% (0.08 g) in THF (0.5 ml) was added at room temperature. The mixture was heated until 50-55° C. for 20-24 h. Then, the mixture was cooled down, the organic layer was washed with a solution of AcOH in water and then filtered off and the solid was extracted with THF. The organic phase was concentrated by evaporation under vacuum and chromatographed on silica gel. 0.26 g of Estetrol (I) were collected. The ratio between the α-15,16-diol and β-15,16-diol is 99/1.

Example 15

Preparation of Estetrol (I)

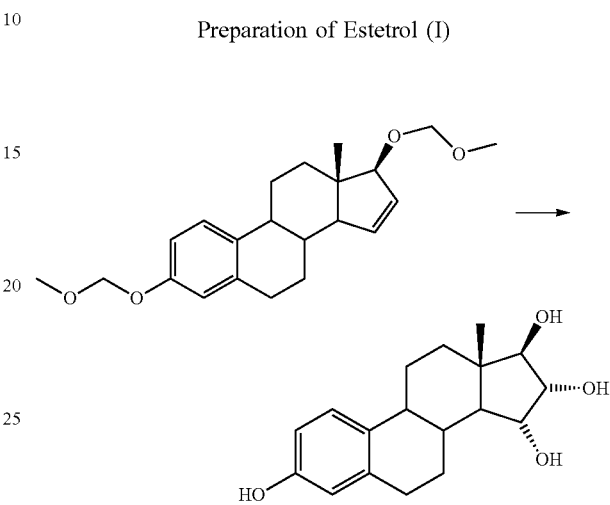

Over the solution of example 12 containing 3,17-methoxy methyl ether-3,17β-dihydroxy-Δ-15-estradiol (0.15 g) and THF (1.5 ml), trimethylamine N-oxide (0.08 g) were added at room temperature. PVP-OsO 4 1% (0.04 g) in THF (0.3 ml) was added at room temperature. The mixture was heated until 50-55° C. for 20-24 h. Then, the mixture was cooled down, the organic layer was washed with a solution of HCl in water and then filtered off and the solid was extracted with THF. The organic phase was concentrated by evaporation under vacuum and chromatographed on silica gel. 0.12 g of Estetrol (I) were collected. The ratio between the α-15,16-diol and β-15,16-diol is 99/1.

Example 16

Preparation of 3,17β-diTHP-Δ-15-estradiol

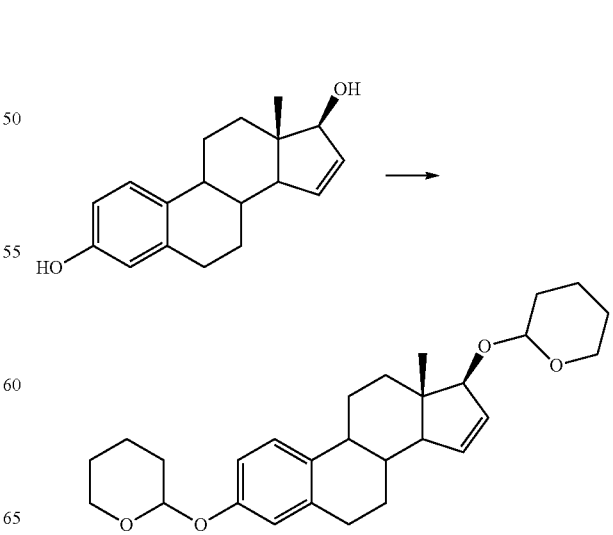

3-17β-dihydroxy-Δ-15-estradiol (12.0 g) was dissolved in 120 ml of dichlormethane, 1.21 g of molecular sieves under inert atmosphere at 5° C. Then p-toluenesulphonic acid (0.41 g) and 16.2 mL of 3,4-Dihydro-2H-pyran were added. The reaction mixture was stirred at room temperature until completion of the reaction was observed by HPLC. Then Triethylamine (1.2 mL) was added. The resulting mixture was filtered off and was washed with water (60 mL twice). The aqueous phase was extracted with 60 ml of dichlormethane. The organic phases were mixed and evaporated under reduced pressure and Methanol was added (60 ml×3 times) and evaporated under reduced pressure. The suspended solid was filtered and washed with Methanol and dried in an oven at 50° C. to yield 17.13 g (88% molar).

NMR-H[1]: 7.19 (1H); 6.84 (1H); 6.80 (1H); 5.97 (1H); 5.79 (1H); 5.39 (1H); 4.74 (1H); 4.37 (1H); 3.93 (2H); 3.58 (2H); 2.88 (2H); 2.27 (2H); 2.15-1.35 (19H); 0.89 (3H).

Example 17

Preparation of Estetrol (I)

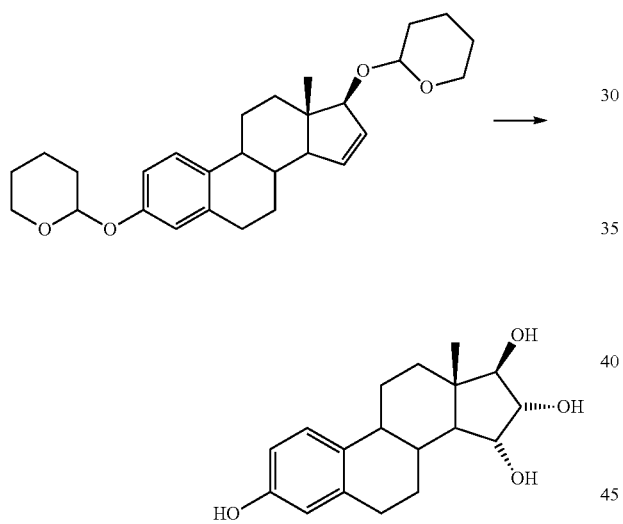

To a stirred solution of 3,17β-diTHP-Δ-15-estradiol (2.5 g), Fibrecat 3003 (0.1 g), N-Methylmorpholine N-oxide (0.8 g) and THF (12.5 ml) were added at room temperature. The mixture was stirred at room temperature until completion of the reaction was observed by HPLC. Then, the mixture was cooled down, filtered off and the organic layer was washed with a solution of $Na_2SO_3$ in water, then the organic layer was washed with a solution of NaCl and then evaporated under reduced pressure. Methanol was added and evaporated under reduced pressure.

Then p-toluenesulphonic acid was added to the resulting mixture until pH 4 and the mixture was heated at 40° C. until completion of the reaction was observed by HPLC.

The organic phases were cooled and evaporated under reduced pressure and Isopropyl ether was added and evaporated under reduced pressure. The suspended solid was filtered and washed with Isopropyl ether and dried in an oven at 50° C. to yield 0.75 g (40% molar from 3-17β-dihydroxy-Δ-15-estradiol).

The ratio between the 15α,16α-diol and 15β,16β-diol is 98/2.

The invention claimed is:

1. A compound of formula (IV)

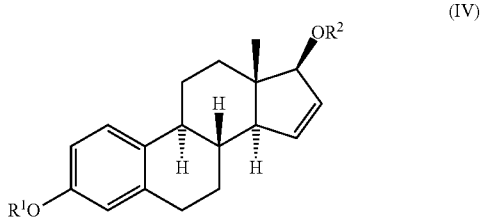

or a salt or solvate thereof, wherein $R^1O$ is a protected hydroxyl group selected from the group consisting of a silyl ether, an ether, an ester, a carbamate and a carbonate, $R^2O$ is a protected hydroxyl group which is an ether, with the proviso that the ether in $R^2O$ does not include silyl ether;

with the proviso that if $R^1O$ is a methyl ether, then $R^2O$ is neither a 2-propynyl ether nor a 2-tetrahydropyranyl ether.

2. A compound, according to claim 1, selected from

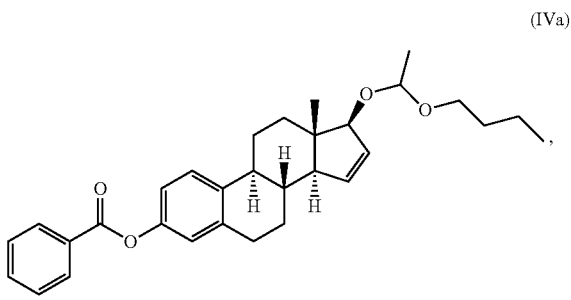

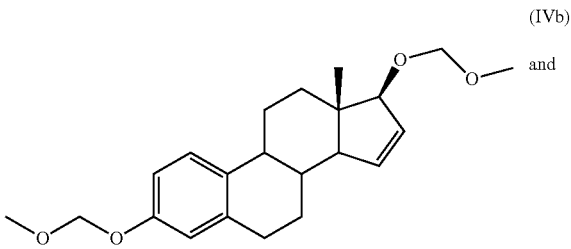

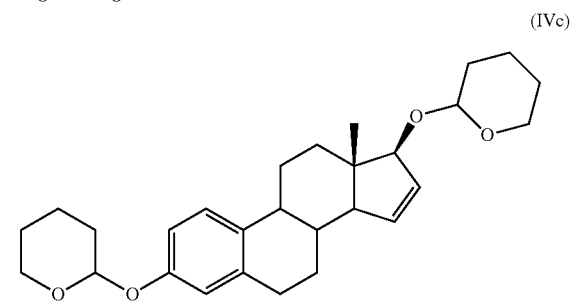

or a salt or solvate thereof.

3. A process for the preparation of Estetrol or a salt or solvate thereof, the process comprising:
a) reacting a compound of formula (IV)

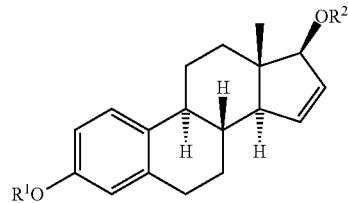

(IV)

or a salt or solvate thereof, wherein
R¹O at position C3 is a protected hydroxyl group selected from the group consisting of a silyl ether, an ether, an ester, a carbamate and a carbonate,
R²O at position C17 is a protected hydroxyl group which is an ether,
with the proviso that the ether in R²O does not include silyl ether;
with an oxidizing agent selected from OsO₄ or a source of osmium tetroxide to produce Estetrol or a compound of formula (II) or a salt or solvate thereof

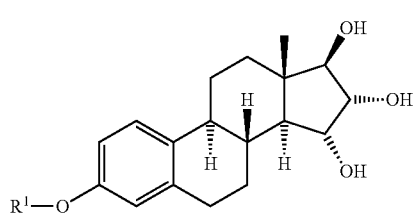

(II)

wherein R¹ is as defined previously; and
b) if a compound of formula (II) is obtained in step a), deprotecting said compound to produce Estetrol.

4. The process according to claim 3, wherein the oxidizing agent is supported.

5. The process according to claim 3, wherein the oxidizing agent is OsO₄-PVP (poly(4-vinyl-pyridine)).

6. The process according to claim 3, wherein a co-oxidant is further added.

7. The process according to claim 3, wherein trimethylamine-N-oxide is added as co-oxidant.

8. The process according to claim 3, wherein the 15β,16β-diol isomer is obtained in an amount ≤3% with respect to the sum of 15β,16β-diol and 15α,16α-diol.

9. The process according to claim 3, wherein the protected hydroxyl group at position C17 in the compound of formula (IV) is an ether selected from (1-butoxyethyl) ether, tetrahydropyranyl (THP) ether, phenylthiomethyl (PTM) ether, and methoxymethyl (MOM) ether.

10. The process according to claim 3, wherein the protected hydroxyl group at position C3 in the compound of formula (IV) is an ester.

11. The process according to claim 3, wherein the protected hydroxyl group at position C3 in the compound of formula (IV) is a benzoyl ester.

12. The process according to claim 3, wherein the protected hydroxyl group at position C3 in the compound of formula (IV) is a benzoyl ester and the protected hydroxyl group at C17 is a (1-butoxyethyl) ether.

13. The process according to claim 3, wherein the protected hydroxyl group at position C3 in the compound of formula (IV) is an ether.

14. The process according to claim 13, wherein the protected hydroxyl group at position C3 in the compound of formula (IV) is an ether selected from (1-butoxyethyl) ether, tetrahydropyranyl (THP) ether, phenylthiomethyl (PTM) ether, and methoxymethyl (MOM) ether.

15. The process according to claim 13, wherein the protected hydroxyl groups at positions C3 and C17 are each an ether independently selected from the group consisting of an alkoxy or aryloxy alkyl ether or an alkyl or aryl thioalkyl ether.

16. The process according to claim 15, wherein the protected hydroxyl groups at positions C3 and C17 are each methoxymethyl (MOM) ether or tetrahydropyranyl (THP) ether.

* * * * *